(12) United States Patent
Keillor et al.

(10) Patent No.: US 9,958,452 B2
(45) Date of Patent: May 1, 2018

(54) HIGHLY FLUOROGENIC PROTEIN LABELLING AGENTS

(71) Applicant: UNIVERSITY OF OTTAWA, Ottawa (CA)

(72) Inventors: Jeffrey Keillor, Ottawa (CA); Yingche Chen, Edmonton (CA)

(73) Assignee: UNIVERSITY OF OTTAWA, Ottawa (CA)

( * ) Notice: Subject to any disclaimer, the term of this patent is extended or adjusted under 35 U.S.C. 154(b) by 0 days. days.

(21) Appl. No.: 15/378,400

(22) Filed: Dec. 14, 2016

(65) Prior Publication Data
US 2017/0168064 A1  Jun. 15, 2017

Related U.S. Application Data

(60) Provisional application No. 62/267,049, filed on Dec. 14, 2015.

(51) Int. Cl.
| C07K 1/13 | (2006.01) |
| G01N 33/58 | (2006.01) |
| C09B 69/00 | (2006.01) |
| C09K 11/06 | (2006.01) |

(52) U.S. Cl.
CPC ............. *G01N 33/582* (2013.01); *C07K 1/13* (2013.01); *C09B 69/001* (2013.01); *C09K 11/06* (2013.01); *C09K 2211/1022* (2013.01); *C09K 2211/1029* (2013.01)

(58) Field of Classification Search
CPC ................................. G01N 33/582; C07K 1/13
See application file for complete search history.

(56) References Cited

U.S. PATENT DOCUMENTS

| 7,700,375 B2 | 4/2010 | Keillor et al. |
| 7,897,787 B2 | 3/2011 | Matsumoto et al. |
| 8,835,641 B2 | 9/2014 | Keillor et al. |
| 9,006,459 B2 | 4/2015 | Keillor et al. |
| 2004/0171014 A1 | 9/2004 | Smith |
| 2006/0147948 A1 | 7/2006 | Keillor et al. |
| 2012/0171665 A1 | 7/2012 | Keillor et al. |
| 2015/0316557 A1 | 11/2015 | Keillor et al. |
| 2016/0282356 A1 | 9/2016 | Keillor et al. |

OTHER PUBLICATIONS

Caron, Karine et al., "Dramatic Increase of Quench Efficiency in "Spacerless" Dimaleimide Fluorogens", Organic & Biomolecular Chemistry, 2011, vol. 9, pp. 185-197.
Chen, Yingche et al., "Coumarin-Based Fluorogenic Probes for No-Wash Protein Labeling", Angewandte Chemie International Edition, 2014, vol. 53, pp. 13785-13788.
Girouard, Stéphane et al., "Synthesis and Characterization of Dimaleimide Fluorogens Designed for Specific Labeling of Proteins", J. Am. Chem. Soc., 2005, vol. 127, pp. 559-566.
Guy, Julia et al., "Convergent Preparation and Photophysical Characterization of Dimaleimide Dansyl Fluorogens: Elucidation of the Maleimide Fluorescence Quenching Mechanism", J. Am. Chem. Soc., 2007, vol. 129, pp. 11969-11977.

(Continued)

*Primary Examiner* — Shawquia Jackson
(74) *Attorney, Agent, or Firm* — BCF LLP

(57) ABSTRACT

There are provided fluorogenic labelling agents comprising a dimaleimide core connected to a BODIPY-based fluorophore, processes for preparation thereof, and uses thereof for labelling and/or detection of specific protein targets. Fluorogenic labelling agents having an excitation wavelength that can be visualized in the green or red channels of fluorescence microscopes are provided. In some embodiments, fluorogenic labelling agents comprising a compound having the structure of Formula I or II, and salts thereof, are described.

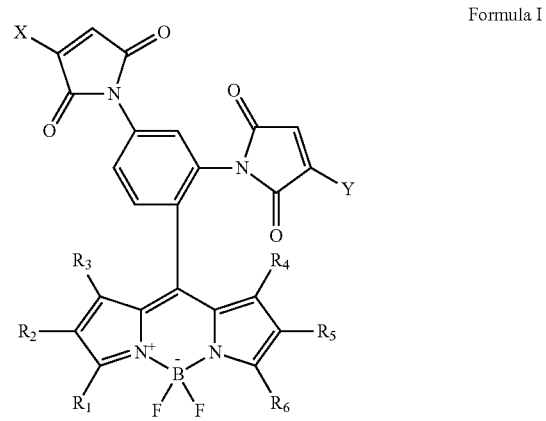

Formula I

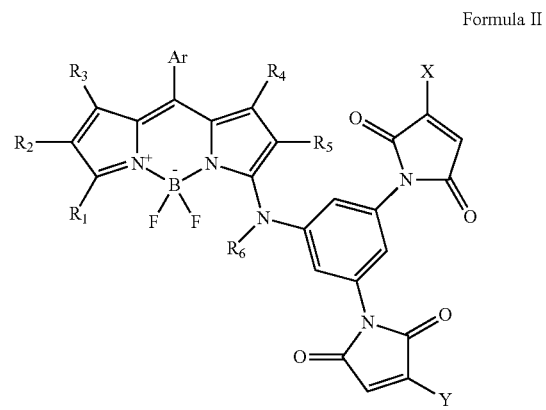

Formula II

23 Claims, 12 Drawing Sheets

(56) References Cited

OTHER PUBLICATIONS

Guy, Julia et al., "De Novo Helical Peptides as Target Sequences for a Specific, Fluorogenic Protein Labelling Strategy", Molecular Biosystems, 2010, vol. 6, pp. 976-987.
Honda, Kazumasa et al., "Evaluation of Fluorescent Compounds for Peroxyoxalate Chemiluminescence Detection", Analytica Chimica Acta, 1985, vol. 177, pp. 111-120.
Kanaoka, Yuichi et al., "Studies on Protein-Sulfhydryl Reagents. I. Synthesis of Benzimidazole Derivatives of Maleimide; Fluorescent Labeling of Maleimide", Chemical & Pharmaceutical Bulletin, 1964, vol. 12, No. 2, pp. 127-134.
Kellner, Stefanie et al., "Structure-Function Relationship of Substituted Bromomethylcoumarins in Nucleoside Specificity of RNA Alkylation", Plos One, 2013, vol. 8, Issue 7, pp. 1-10.
Langmuir, Margaret et al., "New Naphthopyranone Based Fluorescent Thiol Probes", Tetrahedron Letters, 1995, vol. 36, No. 23, pp. 3989-3992.
Meimetis, Labros G. et al., "Ultrafluorogenic Coumarin—Tetrazine Probes for Real-Time Biological Imaging", Angewandte Chemie International Edition, 2014, vol. 53, pp. 7531-7534.
Liang, F. et al. "Gene index analysis of the human genome estimates approximately 120,000." Nat. Genet. 2000, 25, 239-240.
Roest Crollius, H. et al. "Estimate of human gene number provided by genome-wide analysis using." Nat. Genet. 2000, 25, 235-238.
Ewing, B. et al. "Analysis of expressed sequence tags indicates 35,000 human genes." Nat. Genet. 2000, 25, 232-234.
Haughland, R. P. "Handbook of Fluorescent Probes and Research Chemicals." Molecular Probes. Eugene. Oreg. 1992, 5th Edn.
Sippel, T. O. "New fluorochromes for thiols: maleimide and iodoacetamide derivatives of 3-phenyl coumarin fluorophore." J. Histochem. Cytochem. 1981, 29, 314-316.
Corrie, J. E. T. "Thiol-reactive Fluorescent Probes for Protein Labelling." J. Chem. Soc. Perkin Trans. 1, 1994, 2975-2982.
Zhang, J. et al. "Creating New Fluorescent Probes for Cell Biology." Nature Rev. 2002, 3, 906-918.
Tsien, R. Y. "The Green Fluorescent Protein." Annu. Rev. Biochem. 1998, 67, 509-544.
Griffin, B. A. et al. "Specific Covalent Labeling of Recombinant Protein Molecules Inside Live Cells." Science 1998, 281, 269-272.
Griffin, B. A. et al. "Fluorescent labeling of recombinant proteins in living cells with FlAsH." Methods Enzymol. 2000, 327, 565-578.
Gaietta, G. et al. "Multicolor and Electron Microscopic Imaging of Connexin Trafficking." Science 2002, 296, 503-507.
Girouard, S. et al. "Elaboration d'un fluorophore permettant une étude d'apposition protéique." M. Sc. Thesis. Université de Montréal, 2000.
Houle, M. H. et al. "Synthese d'un compose fluorogenique permettant l'étude de l'apposition protéique." M. Sc. Thesis. Université de Montréal. 2003.
Yang, J. R. et al. "Synthesis and Properties of a Maleimide Fluorescent Thiol Reagent Derived a Naphtopyranone." J. Heterocyclic Chem. 1991, 28, 1177.
Russo, A. et al. "Detection and quantitation of biological sulfhydryls." Methods Biochem. Anal. 1988, 33, 165-241.
Pace et al., "A Helix Propensity Scale Based on Experimental Studies of Peptides and Proteins", Biophysical Journal, 1998, vol. 75, pp. 422-427.
Matsumoto T. et al., "A Thiol-Reactive Fluorescence Probe Based on Donor-Excited Photoinduced Electron Transfer: Key Role of Ortho Substitution", American Chemical Society, Organic Letters, 2007, vol. 9, No. 17, pp. 3375-3377.
Fisher et al., "Transglutaminase interacts with a6/b4-integrin to stimulate Hippo-dependent *Np63a stabilization leading to enhanced epidermal cancer stem cell survival", Department of Biochemistry and Molecular Biology.
Kerr et al., "Transamidase site-targeted compounds alter the conformation of transglutaminase to reduce GTP binding activity and cancer stem cell survival", Department of Biochemistry and Molecular Biology.
Fisher et al., "Transglutaminase us required for epidermal squamous cell carcinoma stem cell survival", Department of Biochemistry and Molecular Biology.
Fisher et al., "Type II transglutaminase stimulates epidermal cancer stem cell epithelial-mesenchymal transition", Oncotarget, Advance Publications, 2015, pp. 1-15.
Caron, "Développement d'une méthode de marquage protéique par fluorescence", Université De Montréal, 2009.

Non-fluorescent
BODIPY dimaleimide
fluorogen

Regioselective
Non-fluorescent
adduct

Fluorescent adduct
800-fold FE

BODIPY dimaleimide
fluorogen
(*non-fluorescent*)

labelled protein adduct
(*several hundred-fold
more fluorescent*)

a) YC28 b) YC29

(a)

(b)

US 9,958,452 B2

HIGHLY FLUOROGENIC PROTEIN LABELLING AGENTS

CROSS-REFERENCE TO RELATED APPLICATIONS

This application claims priority to U.S. Provisional Application No. 62/267,049 filed Dec. 14, 2015, the entire contents of which are hereby incorporated by reference.

FIELD

The present disclosure broadly relates to novel fluorogenic labelling agents. More specifically, but not exclusively, the present disclosure relates to fluorescent labelling agents comprising a dimaleimide core connected to a BODIPY-based fluorophore and to a process for the preparation of such BODIPY-based fluorogenic agents. The present disclosure also relates to the use of such fluorescent markers for the labelling and detection of specific protein targets.

BACKGROUND

The sequencing of the human genome has allowed the identification of a vast number of putative genes. However, the function of only a small number of these genes can be inferred from their primary sequences. New techniques and agents are needed to cope with the task of assigning functional roles to these gene products. This implies determination of how, when and where they are involved in specific biochemical pathways. Ideally, these techniques and agents will allow the rapid screening of substantial subsets of the sum of a genome's products. Some methods have been designed for broad and rapid screening, but they are generally limited to in vitro application and do not necessarily provide information that is relevant to the function of proteins in living cells. Visualizing and monitoring specific proteins, with minimal disruption of their biological function and distribution, remains one of the foremost challenges in chemical biology. More powerful methods of detection of specific proteins and monitoring their localization and interactions inside living cells are urgently required.

One of the most widely applied methods for studying the expression, localization and trafficking of cellular proteins is the fluorescent labelling of a specific protein of interest (POI). This can be accomplished by genetically fusing the POI to an intrinsically fluorescent protein, or to an enzyme that can be labelled with a fluorescent inhibitor. However, the significant size of these fusion proteins can alter the biological function of the POI. Alternatively, a POI can be fused to a 'substrate tag' that can be site-specifically labelled through a subsequent enzymatic reaction. In this approach, the smaller size of the tag poses less risk for steric perturbation than the fusion of an entire protein; however, native enzymatic reactions can prove to be problematic for some cellular applications.

Maleimide groups have long been used in applications that exploit their propensity to react selectively with thiol groups, undergoing Michael addition reactions through their C2=C3 double bond (Kanaoka, Y. et al., Chem. Pharm. Bull. 1964, 12, 127). Maleimides are also known to quench fluorescence, probably due to their participation in a photoinduced electron transfer (PeT), allowing non-radiative relaxation of the fluorophore's excited state. The thiol addition reaction breaks the conjugation of the maleimide group, altering the energy levels of its molecular orbitals and removing its capacity to quench fluorescence (Guy, J. et al., J. Am. Chem. Soc. 2007, 129, 11969). These properties were demonstrated in the characterization of a naphthopyranone derivative bearing a maleimide group whose fluorescence increased dramatically upon reaction with glutathione (Langmuir, M. E. et al., Tetrahedron Lett. 1995, 36, 3989).

Labelling techniques based on the use of fluorescent dyes bearing reactive functional groups like maleimides, known to react with thiols, have been described (Tsien, R. Y., Annu. Rev. Biochem. 1998, 67, 509-544). However, these methods are typically non-specific, labelling the surface-exposed functional groups of many different proteins. Based on this chemical reaction, we previously developed a complementary labelling strategy based on the Fluorogenic Addition Reaction (FlARe) between a small, genetically encoded dicysteine peptide tag and dimaleimide fluorogenic labelling agents. In the FlARe approach to protein labelling, a POI is genetically fused to a short peptide tag (dC10α) presenting two Cys residues that are separated by two turns of the α-helical secondary structure of the tag, placing them ca. 10 Å apart. Fluorogenic labelling agents have also been designed, presenting two maleimide groups separated by ca. 10 Å that can react with the thiol groups of the dC10α tag sequence. The dimaleimide moiety quenches the fluorescence of the pendant fluorophore through a PeT mechanism, until both maleimide groups undergo thiol addition. The addition reactions restore the latent fluorescence and result in robust, covalent labelling (Keillor, J. W. et al., Org Biomol Chem 2011, 9, 185-197; Keillor, J. W. et al., Mol Biosyst 2010, 6, 976-987; Keillor, J. W. et al., J Am Chem Soc 2007, 129, 11969-11977; Girouard, S. et al., J Am Chem Soc 2005, 127, 559-566). Using the FlARe approach, we were able to selectively label the POI.

Recently we refined the design of the dimaleimide fluorogens to enhance quench efficiency and the reactivity of the maleimide group, as demonstrated through selective no-wash intracellular labelling (Caron, K. et al., Org Biomol Chem 2011, 9, 185-197; Chen, Y. et al., Angew Chem Int Ed Engl 2014). However, known fluorogens include dansyl and coumarin groups, both of which require excitation with UV or blue light, raising questions regarding the risk of photodamage. There is a need for fluorogens with longer excitation wavelength that can be visualized in the green and red channels of fluorescence microscopes for use in FlARe labelling strategies.

SUMMARY

It is an object of the present invention to ameliorate at least some of the deficiencies present in the prior art. Embodiments of the present technology have been developed based on the inventors' appreciation that there is a need for improved fluorogenic compounds for labelling POIs.

We report herein the design and synthesis of fluorogens with long excitation and emission wavelengths, based on the BODIPY fluorophore, for intracellular applications such as FlARe labelling. The expression "long wavelength" is used herein to refer to wavelengths longer than the wavelength of blue light. The PeT quenching mechanism poses distinct challenges for the design of long wavelength probes, whose excited states are typically low in energy. We provide for the first time novel FlARe fluorogenic agents for intracellular labelling that emit long wavelength light (e.g., green or red light). In some embodiments, these fluorogenic agents can be visualized in the green and red channels of fluorescence microscopes and have wide application as intracellular labelling agents, allowing the FlARe labelling strategy to be extended to several of the channels common to fluorescent microscopes.

The present disclosure relates broadly to novel long-wavelength fluorogenic labelling compounds comprising a dimaleimide core connected to a BODIPY-based fluorophore that emit at long wavelengths such as red and green, and to processes for the preparation of such fluorogenic labelling compounds and uses thereof. Compounds have been screened for their selectivity for POI labelling. In one embodiment of the invention, there are provided BODIPY-based "turn-on" fluorogens that exhibit negligible background reactivity and/or high selectivity for site-specific protein labelling, and uses thereof for the labelling and detection of specific protein targets. In some embodiments, fluorogenic compounds provided herein are capable of intracellular application, for example to fluorescently label specific proteins in living cells.

In a first broad aspect, there are provided "green" BODIPY-based fluorogenic, protein-specific labelling agents. The term "green" is used to refer to fluorogenic agents that emit green light. Such agents are typically visible using the green channel on a fluorescent microscope. These agents are dimaleimide derivatives that undergo a Fluorogenic Addition Reaction (FlARe) with a genetically encodable peptide tag (e.g., dC10α). The application of this reaction for the fluorogenic labelling of specific proteins of interest (POIs) in SDS-PAGE gels and inside living cells is also provided herein.

In an embodiment, there is provided a fluorogenic labelling agent of Formula I, or a salt thereof:

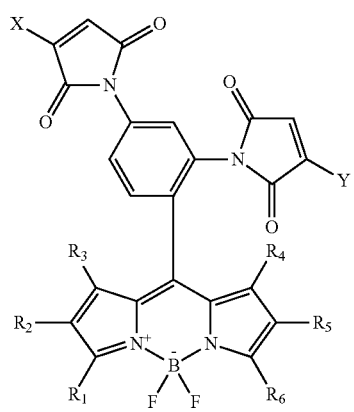

Formula I wherein:
$R_1$, $R_2$, $R_3$, $R_4$, $R_5$, and $R_6$ are independently selected from hydrogen, alkyl, alkenyl, alkynyl, cycloalkyl, cycloalkenyl, cycloalkynyl, aryl, alkaryl, arylalkyl, carboxy alkyl, aryl, heterocyclic, heteroaryl, and heteroaromatic, alkyl being optionally substituted by hydroxyl, amino, carboxyl, carboxylic ester, sulfonate, amide, carbamate, or aminoalkyl; and X and Y are independently $R_7$ or $OR_8$, wherein $R_7$ is selected from hydrogen, halogen, and alkyl, alkyl being optionally substituted by hydroxyl, amino, carboxyl, carboxylic ester, amide, carbamate, or aminoalkyl, and $R_8$ is alkyl, alkyl being optionally substituted by hydroxyl, amino, carboxyl, carboxylic ester, sulfonate, amide, carbamate, or aminoalkyl.

In some embodiments of Formula I, alkyl, alkenyl, alkynyl, cycloalkyl, cycloalkenyl, cycloalkynyl, aryl, alkaryl, arylalkyl, carboxy alkyl, aryl, heterocyclic, heteroaryl, or heteroaromatic are unsubstituted. In other embodiments of Formula I, alkyl, alkenyl, alkynyl, cycloalkyl, cycloalkenyl, cycloalkynyl, aryl, alkaryl, arylalkyl, carboxy alkyl, aryl, heterocyclic, heteroaryl, or heteroaromatic may be substituted by hydroxyl, amino, carboxyl, sulfonate, carboxylic ester, amide, carbamate, or aminoalkyl.

In an embodiment of Formula I, at least one of X and Y is $OR_8$. In another embodiment of Formula I, when one of X and Y is $OR_8$, then the other is $R_7$. In other words, in an embodiment of Formula I, when X is $OR_8$, Y is $R_7$. In another embodiment of Formula I, when Y is $OR_8$, X is $R_7$. In some embodiments of Formula I, X and Y are the same. In some embodiments of Formula I, $R_7$ and $R_8$ are the same. In some embodiments of Formula I, $R_7$ and $R_8$ are different.

In an embodiment of Formula I, X and Y are both $OR_8$. In an embodiment of Formula I, X and Y are both $OR_8$ where $R_8$ is alkyl. In an embodiment of Formula I, X and Y are both methoxy ($O—CH_3$).

In an embodiment of Formula I, $R_1$, $R_2$, $R_3$, $R_4$, $R_5$, and $R_6$ are the same. In an embodiment of Formula I, $R_1$, $R_2$, $R_3$, $R_4$, $R_5$, and $R_6$ are different. In an embodiment of Formula I, $R_2$ and $R_5$ are the same, and $R_1$, $R_3$, $R_4$, and $R_6$ are the same.

In an embodiment of Formula I, $R_1$, $R_2$, $R_3$, $R_4$, $R_5$, and $R_6$ are independently selected from hydrogen and alkyl. In an embodiment of Formula I, $R_2$ and $R_5$ are hydrogen and $R_1$, $R_3$, $R_4$, and $R_6$ are alkyl. In an embodiment of Formula I, $R_2$ and $R_5$ are hydrogen and $R_1$, $R_3$, $R_4$, and $R_6$ are methyl. In an embodiment of Formula I, $R_1$, $R_2$, $R_3$, $R_4$, $R_5$, and $R_6$ are hydrogen. In an embodiment of Formula I, one or both of $R_1$ and $R_6$ are amide or carboxylic acid. In an embodiment of Formula I, one or both of $R_2$ and $R_5$ are alkyl.

In a second broad aspect, there are provided "red" BODIPY-based fluorogenic, protein-specific labelling agents. The term "red" is used to refer to fluorogenic agents that undergo excitation with light in the orange-to-red spectrum. Such agents are typically visible using the red channel on a fluorescent microscope. These agents are dimaleimide derivatives that undergo a Fluorogenic Addition Reaction (FlARe) with a genetically encodable peptide tag (e.g., dC10α). The application of this reaction for the fluorogenic labelling of specific proteins of interest (POIs) in SDS-PAGE gels and inside living cells is also provided herein.

In an embodiment, there is provided a fluorogenic labelling agent of Formula II, or a salt thereof:

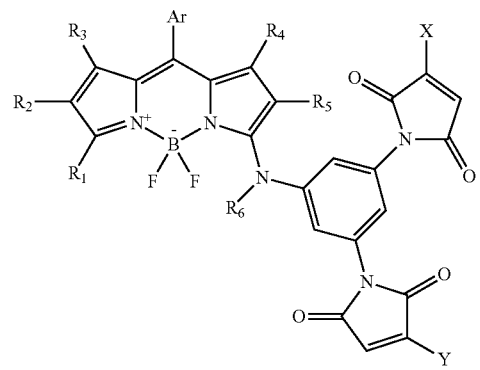

Formula II wherein:

R$_1$ is hydrogen, R$_1$', SR$_1$', OR$_1$' or NR$_2$'R$_3$', wherein R$_1$', R$_2$' and R$_3$' are independently selected from hydrogen, alkyl, alkenyl, alkynyl, cycloalkyl, cycloalkenyl, cycloalkynyl, aryl, alkaryl, arylalkyl, and carboxy alkyl, alkyl being optionally substituted by hydroxyl, amino, carboxyl, carboxylic ester, sulfonate, amide, carbamate, or aminoalkyl; or R$_1$' and R$_2$ or R$_1$' and R$_3$ come together to form a 5, 6 or 7-membered ring which is selected from aryl, heterocyclic, heteroaryl, and heteroaromatic; or R$_2$', R$_2$, R$_3$', and R$_3$ come together independently to form at least one 5, 6 or 7-membered ring which is selected from aryl, heterocyclic, heteroaryl and heteroaromatic;

R$_2$, R$_3$, R$_4$, R$_5$ and R$_6$ are independently selected from hydrogen, alkyl, alkenyl, alkynyl, cycloalkyl, cycloalkenyl, cycloalkynyl, aryl, alkaryl, arylalkyl, carboxy alkyl, aryl, heterocyclic, heteroaryl, and heteroaromatic, alkyl being optionally substituted by hydroxyl, amino, carboxyl, sulfonate, carboxylic ester, amide, carbamate, or aminoalkyl;

X and Y are independently R$_7$ or OR$_8$, wherein R$_7$ is selected from hydrogen, halogen, and alkyl, alkyl being optionally substituted by hydroxyl, amino, carboxyl, carboxylic ester, sulfonate, amide, carbamate, or aminoalkyl, and R$_8$ is alkyl, alkyl being optionally substituted by hydroxyl, amino, carboxyl, carboxylic ester, sulfonate, amide, carbamate, or aminoalkyl; and Ar is aryl, heterocyclic, heteroaryl, or heteroaromatic and is optionally substituted by alkyl, cycloalkyl or halogen, alkyl being optionally substituted with hydroxyl, amino, carboxyl, sulfonate, carboxylic ester, amide, carbamate, or aminoalkyl.

In some embodiments of Formula II, alkyl, alkenyl, alkynyl, cycloalkyl, cycloalkenyl, cycloalkynyl, aryl, alkaryl, arylalkyl, carboxy alkyl, aryl, heterocyclic, heteroaryl, or heteroaromatic are unsubstituted. In other embodiments of Formula II, alkyl, alkenyl, alkynyl, cycloalkyl, cycloalkenyl, cycloalkynyl, aryl, alkaryl, arylalkyl, carboxy alkyl, aryl, heterocyclic, heteroaryl, or heteroaromatic may be substituted by hydroxyl, amino, carboxyl, sulfonate, carboxylic ester, amide, carbamate, or aminoalkyl.

In some embodiments of Formula II, Ar is phenyl, pyridine, pyrimidine or triazine and is optionally substituted by alkyl, cycloalkyl or halogen, alkyl being optionally substituted with hydroxyl, amino, carboxyl, sulfonate, carboxylic ester, amide, carbamate, or aminoalkyl.

In an embodiment of Formula II, at least one of X and Y is OR$_8$. In another embodiment of Formula II, when one of X and Y is OR$_8$, then the other is R$_7$. In other words, in an embodiment of Formula II, when X is OR$_8$, Y is R$_7$. In another embodiment of Formula II, when Y is OR$_8$, X is R$_7$. In some embodiments of Formula II, X and Y are the same. In some embodiments of Formula II, X and Y are different. In some embodiments of Formula II, R$_7$ and R$_8$ are the same. In some embodiments of Formula II, R$_7$ and R$_8$ are different.

In an embodiment of Formula II, X and Y are both OR$_8$. In an embodiment of Formula II, X and Y are both OR$_8$ where R$_8$ is alkyl. In an embodiment of Formula II, X and Y are both methoxy (O—CH$_3$).

In an embodiment of Formula II, R$_2$, R$_3$, R$_4$, and R$_5$ are the same. In an embodiment of Formula II, R$_2$, R$_3$, R$_4$, and R$_5$ are different. In an embodiment of Formula II, R$_2$, R$_3$, R$_4$, R$_5$ and R$_6$ are the same. In an embodiment of Formula II, R$_2$, R$_3$, R$_4$, R$_5$ and R$_6$ are different. In an embodiment of Formula II, R$_2$, R$_3$, R$_4$, R$_5$, and R$_6$ are hydrogen.

In an embodiment of Formula II, R$_1$, R$_2$, R$_3$, R$_4$, R$_5$, and R$_6$ are hydrogen.

In some embodiments of Formula II, R$_1$ is an amino substituent, an oxygen substituent, a sulfur substituent, a thiol ether, or an ester. In some embodiments of Formula II, R$_1$ is hydrogen. In some embodiments of Formula II, R$_1$ is MeO$_2$CCH$_2$S. In some embodiments of Formula II, R$_1$ is NMePh.

In an embodiment of Formula II, R$_1$ is SR$_1$' or OR$_1$' or NR$_2$'R$_3$' as defined above, and R$_2$, R$_3$, R$_4$, R$_5$ and R$_6$ are hydrogen.

In some embodiments, fluorogenic labelling agents provided herein lead to fluorescent labels that emit red, orange, or green light. In some embodiments, fluorogenic labelling agents provided herein have an emission wavelength that can be visualized in the green or red channels of a fluorescence microscope. In some embodiments, fluorogenic labelling agents provided herein provide fluorogens having a longer excitation wavelength than fluorogens that are excited or visualized with UV or blue light.

In an embodiment, there are provided fluorogenic labelling agents comprising one or more compound selected from YC23, YC28, YC29, and salts thereof. The structures of YC23, YC28, and YC29 are as follows:

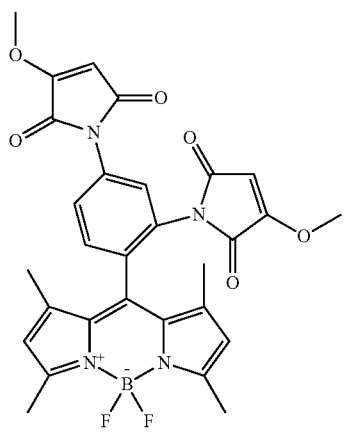

YC23

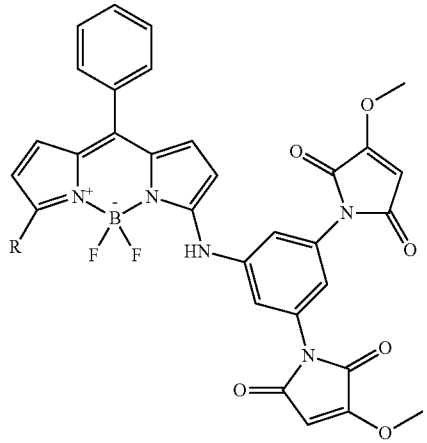

YC28 (R = MeO$_2$CCH$_2$S)
YC29 (R = NMePh)

In some embodiments of the technology, fluorogenic labelling agents are not toxic to animal cells, e.g., fluorogenic labelling agents are not toxic to mammalian cells, invertebrate cells, vertebrate cells, human cells, rodent cells, mouse cells, rat cells, insect cells, nematode cells, or fish cells.

In some embodiments of the technology, a fluorogenic labelling agent's fluorescence is quenched when the fluorogenic labelling agent is in its conjugated form, and not quenched in the form of a thiol adduct. In some embodiments, the fluorescence of the fluorogenic labelling agent increases after reaction with sulfhydryl groups on a protein. In some embodiments, a fluorogenic labelling agent specifically reacts with two Cys residues separated by about 10 Å or with a dC10α tag. In some embodiments, a fluorogenic labelling agent does not react appreciably with cellular proteins or with glutathione (GSH). In some embodiments, a fluorogenic labelling agent has one or more of the following characteristics: aqueous solubility; non-toxic to animal cells; low background fluorescence before reaction with a target protein; increased fluorescence after reaction with a target protein; bright fluorescence after reaction with a target protein; cell permeability; non-reactivity with GSH; and specific binding to two sulfhydryl residues separated by about 10 Å or a dC10α tag.

In an aspect, there are provided herein methods for labelling and/or detecting a target protein, comprising: a) contacting the target protein with a fluorogenic labelling agent provided herein, under conditions where the fluorogenic labelling agent reacts with sterically unhindered sulfhydryl groups on the target protein; and b) detecting a fluorescent signal from the fluorogenic labelling agent, wherein the fluorescence of the fluorogenic labelling agent is quenched in the absence of reaction with the target protein, and detection of the fluorescent signal indicates reaction of the fluorogenic labelling agent with the target protein.

In an embodiment, there are provided methods for labelling and/or detecting a target protein, comprising: a) contacting the target protein with a fluorogenic labelling agent provided herein, under conditions where the fluorogenic labelling agent reacts with sterically unhindered sulfhydryl groups on the target protein; and b) detecting a fluorescent signal from the fluorescent labelling agent, wherein the fluorescence of the fluorogenic labelling agent increases after reaction with the target protein.

In embodiments of methods of the invention, the contacting may occur in vivo, ex vivo, or in vitro. In some embodiments, the contacting may occur in a cultured cell expressing a protein of interest (POI) or target protein. The target protein may be, for example, an intracellular protein, or an extracellular or cell-surface protein. The contacting may occur intracellularly in some embodiments.

In some embodiments, a target protein comprises two Cys residues separated by about 10 Å, e.g., dC10α tag. For example, a target protein may have been genetically engineered to comprise two Cys residues separated by about 10 Å, or a dC10α tag.

There are also provided herein methods for live imaging of a target protein, comprising: a) contacting the target protein with a fluorogenic labelling agent provided herein, under conditions where the fluorogenic labelling agent reacts with sterically unhindered sulfhydryl groups on the target protein; and b) detecting a fluorescent signal from the fluorogenic labelling agent, wherein the fluorescence of the fluorogenic labelling agent increases after reaction with the target protein, or is detectable only after reaction with the target protein. In some embodiments, the target protein has been engineered to comprise two Cysteine residues separated by about 10 Å or a dC10α tag prior to the contacting step.

In a further aspect, there are provided kits for labelling and/or detecting a target protein, comprising a fluorogenic labelling agent provided herein, and instructions for use thereof.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

For a better understanding of the invention and to show more clearly how it may be carried into effect, reference will now be made by way of example to the accompanying drawings, which illustrate aspects and features according to embodiments of the present invention, and in which.

DETAILED DESCRIPTION

Figure 1:
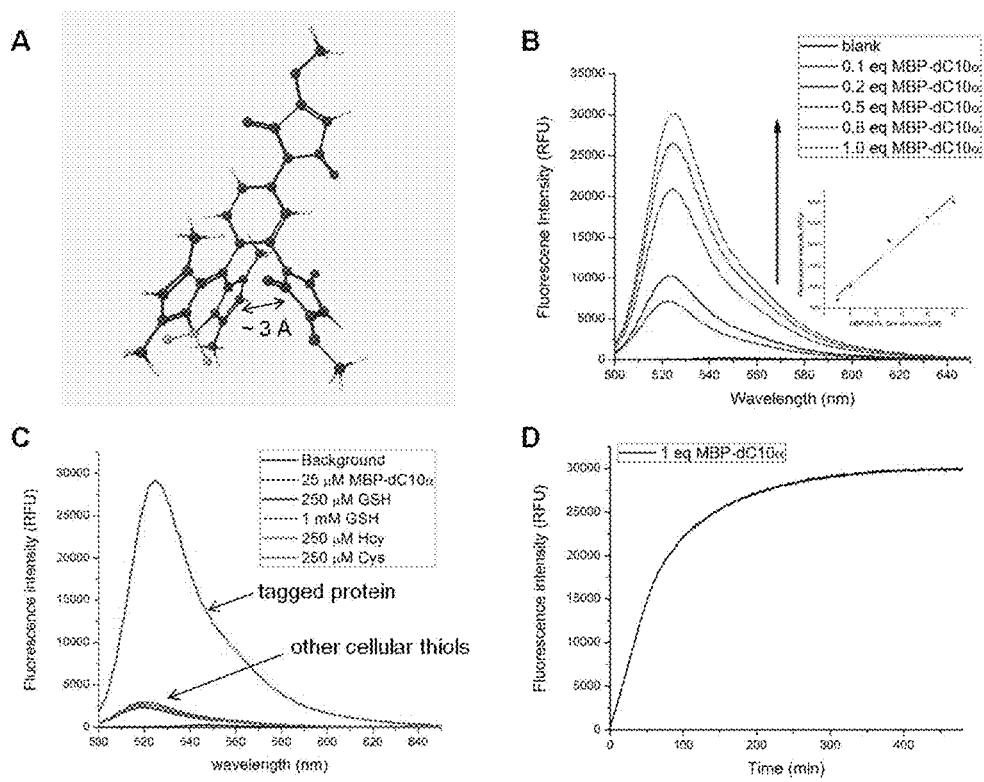
FIG. 1 shows characterization of the fluorogen YC23. (A) shows DFT-minimized geometry of YC23, showing distance between ortho-maleimide and BODIPY groups. (B) shows fluorescence enhancement ($\lambda_{ex}$=480 nm) of 25 μM fluorogen YC23, incubated in the absence (black) and presence of varied concentrations of MBP-dC10α (coloured). The inset shows linear fit of fluorescence intensity of YC23 vs [MBP-dC10α]. (C) shows fluorescence emission spectra ($\lambda_{ex}$=480 nm) of YC23 (25 μM) after overnight reaction with MBP-dC10α (25 μM), GSH (250 μM and 1 mM), Cys (250 μM), or homocysteine (250 μM). (D) shows time-dependent fluorescence ($\lambda_{ex}$=495 nm, $\lambda_{em}$=525 nm) increase of YC23 (25 μM) treated with test protein MBP-dC10α (25 μM). All tests were performed in 50 mM HEPES buffer (pH 7.4).

In order to provide a clear and consistent understanding of the terms used in the present specification, a number of definitions are provided below. Moreover, unless defined otherwise, all technical and scientific terms as used herein have the same meaning as commonly understood to one of ordinary skill in the art to which this invention pertains.

The use of the word "a" or "an" when used in conjunction with the term "comprising" in the claims and/or the specification may mean "one", but it is also consistent with the meaning of "one or more", "at least one", and "one or more than one". Similarly, the word "another" may mean at least a second or more.

As used in this specification and claim(s), the words "comprising" (and any form of comprising, such as "comprise" and "comprises"), "having" (and any form of having, such as "have" and "has"), "including" (and any form of including, such as "include" and "includes") or "containing" (and any form of containing, such as "contain" and "contains"), are inclusive or open-ended and do not exclude additional, unrecited elements or process steps.

The term "about" is used to indicate that a value includes an inherent variation of error for the device or the method being employed to determine the value.

The term "derivative" as used herein, is understood as being a substance similar in structure to another compound but differing in some slight structural detail.

The present description refers to a number of chemical terms and abbreviations used by those skilled in the art. Nevertheless, definitions of selected terms are provided for clarity and consistency.

As used herein, the term "alkyl" can be straight-chain or branched. Examples of alkyl residues containing from 1 to 6 carbon atoms are methyl, ethyl, propyl, butyl, pentyl, hexyl, the n-isomers of all these residues, isopropyl, isobutyl, isopentyl, neopentyl, isohexyl, 3-methylpentyl, sec-butyl, tert-butyl, or tert-pentyl. Alkyl residues may be substituted or unsubstituted. In some embodiments, for example, alkyl may be substituted by hydroxyl, amino, carboxyl, carboxylic ester, amide, carbamate, or aminoalkyl.

As used herein, the term "cycloalkyl" can be monocyclic or polycyclic, for example monocyclic, bicyclic or tricyclic, i.e., they can for example be monocycloalkyl residues, bicycloalkyl residues and tricycloalkyl residues, provided they have a suitable number of carbon atoms and the parent hydrocarbon systems are stable. A bicyclic or tricyclic cycloalkyl residue has to contain at least 4 carbon atoms. In an embodiment, a bicyclic or tricyclic cycloalkyl residue contains at least 5 carbon atoms. In a further embodiment, a bicyclic or tricyclic cycloalkyl residue contains at least 6 carbon atoms and up to the number of carbon atoms specified in the respective definition. Cycloalkyl residues can be saturated or contain one or more double bonds within the ring system. In particular they can be saturated or contain one double bond within the ring system. In unsaturated cycloalkyl residues the double bonds can be present in any suitable positions. Monocycloalkyl residues are, for example, cyclopropyl, cyclobutyl, cyclopentyl, cyclopentenyl, cyclohexyl, cyclohexenyl, cycloheptyl, cycloheptenyl, cyclooctyl, cyclononyl, cyclodecyl, cycloundecyl, cyclododecyl or cyclotetradecyl, which can also be substituted, for example by $C_1$-$C_4$ alkyl. Examples of substituted cycloalkyl residues are 4-methylcyclohexyl and 2,3-dimethylcyclopentyl. Examples of parent structures of bicyclic ring systems are norbornane, bicyclo[2.2.1]heptane, bicyclo[2.2.2]octane and bicyclo[3.2.1]octane.

As used herein, the term "aryl" means an aromatic substituent that is a single ring or multiple rings fused together. When formed of multiple rings, at least one of the constituent rings is aromatic. In an embodiment, aryl substituents include phenyl, naphthyl and anthracyl groups.

The term "heteroaryl", as used herein, is understood as being unsaturated rings of five or six atoms containing one or two O- and/or S-atoms and/or one to four N-atoms, provided that the total number of hetero-atoms in the ring is 4 or less. The heteroaryl ring is attached by way of an available carbon or nitrogen atom. Non-limiting examples of heteroaryl groups include 2-, 3-, or 4-pyridyl, 4-imidazolyl, 4-thiazolyl, 2- and 3-thienyl, and 2- and 3-furyl. The term "heteroaryl", as used herein, is understood as also including bicyclic rings wherein the five or six membered ring containing O, S and N-atoms as defined above is fused to a benzene or pyridyl ring. Non-limiting examples of bicyclic rings include but are not limited to 2- and 3-indolyl as well as 4- and 5-quinolinyl.

In a broad aspect, the present disclosure relates to long-wavelength fluorogens or fluorogenic reagents formed as the combination of a BODIPY derivative and a linker bearing a dimaleimide reactive unit. Compounds presented herein are designed to provide BODIPY fluorophores that demonstrate efficient quenching in their unreacted state and "turn on" when bound to a protein, providing fluorogenic labelling reagents. We report herein the design and synthesis of novel fluorogen compounds based on BODIPY, a commonly used fluorophore, that are capable of excitation at long wavelengths and/or visible by fluorescent microscopes in the green or red channels.

In the FlARe method for intracellular labelling of a protein of interest (POI), the POI is genetically fused to a short peptide tag (dC10α) that presents two Cys residues separated by two turns of an α-helix (ca. 10 Å). These Cys residues can covalently react with a complementary synthetic fluorogenic reagent, thereby turning on its fluorescence and fluorescently labelling the POI. The fluorogenic reagents comprise a fluorophore and a dimaleimide moiety, which has been shown to quench fluorescence by photoinduced electron transfer (PeT) such that the latent fluorescence is restored only after both maleimide groups have undergone their specific thiol addition reactions.

Maleimide groups are known for undergoing specific thiol addition reactions and have been widely applied, although typically non-specifically, in protein labelling. Maleimide groups are also known to quench fluorescence in their conjugated form, but not as their thiol adduct products. Accordingly, fluorogenic labelling agents provided herein are designed to comprise a fluorophore and a dimaleimide moiety, such that their latent fluorescence is quenched by photoinduced electron transfer (PeT) until both maleimide groups undergo specific thiol addition reactions. The quenching efficiency of the dimaleimide allows the fluorogenic labelling agents provided herein to be used as "turn-on" agents whose fluorescence is induced, or "turned-on", upon reaction with a specific POI that has been linked to, e.g., genetically fused to, an appropriate Cysteine-containing tag. It is noted that linkage of the fluorophore and the dimaleimide scaffold is critical for quenching efficiency.

A dimaleimide fluorogen must undergo two thiol addition reactions before its latent fluorescence is restored. For fluorogenic labelling agents provided herein, a fluorescent response is selective for a POI genetically fused to a short peptide sequence that presents two Cys residues, separated by two turns of the α-helix (~10 Å) (such as, for example, a dC10α tag), because very few native proteins present two free Cys residues on their surface, ~10 Å apart. This selectively allows use of the fluorogenic labelling agents specifically to label POIs having an appropriate two-Cysteine tag (such as a dC10α tag).

High specificity and/or absence of non-specific, background reactivity, as well as efficient quenching of fluorescence for an unbound fluorogen, are required in order to provide selective labelling agents capable of intracellular application. Fluorogenic labelling agents provided herein have been designed to increase their selectivity for site-specific protein labelling, reduce their non-specific background reactivity, and/or increase their quenching efficiency, in order to provide improved agents for fluorescent labelling of a specific protein of interest (POI). In an embodiment, fluorogenic labelling agents provided herein demonstrate sufficiently high selectivity, sufficiently low background reactivity, and/or sufficiently efficient quenching that they can be used for intracellular labelling of a specific POI.

Fluorogenic labelling agents described herein provide some or all of the following advantages: First, in some embodiments, they are highly specific for target protein labelling; even in the presence of high concentrations of GSH or other thiol compounds, they do not react to give an increased fluorescent signal. Thus, they can be used for intracellular labelling, where other fluorogens that do not show this high specificity cannot be used. It is noted that some dimaleimide fluorogens which have been described previously demonstrate lower specificity and/or higher background reactivity and are therefore not suitable for intracellular labelling (presumably because a dimaleimide fluorogen could react with one Cys residue of an adventitious protein followed by a reaction with one equivalent of the ubiquitous GSH, or with two equivalents of GSH, leading to a non-specific fluorogenic reaction). Thus, in some embodiments, fluorogenic labelling agents presented herein are improved as compared to other dimaleimide fluorogens that have been described, having improvement in one or more of the following characteristics: specificity; background reactivity; and quenching efficiency. Second, in some embodiments, fluorogenic labelling agents provided herein are non-toxic, which makes them advantageous for cellular application and safer to use than other known labelling agents such as, for example, organoarsenic compounds (e.g., "FlAsH" labelling agents). Third, in some embodiments, fluorogenic labelling agents provide highly efficient quenching of latent fluorescence of the fluorophore. In some embodiments, the latent fluorescence of the fluorophore (i.e., fluorescence before reaction with the POI, or before labelling) is fully quenched. In some embodiments, the latent fluorescence is fully quenched, and the fluorogen nevertheless produces a strong fluorescent signal after labelling or reaction with a POI. The fluorogenic labelling agents provided herein are based on BODIPY and derivatives thereof; in some embodiments, the latent fluorescence of BODIPY or a BODIPY derivative is fully quenched, and the fluorogens give strong fluorescent signal after labelling. Fourth, with BODIPY or a derivative thereof as fluorophore, fluorogenic labelling agents are not sensitive to the protein labelling environment and are amenable to fluorescence microscopy experiments, since their excitation and emission correlate with the filter sets available in most fluorescence microscopes.

In addition, fluorogenic labelling agents described herein may possess some or all of the following advantages of dimaleimide compounds: 1) the dicysteine tags used in the methods of the present disclosure have a far smaller potential to disrupt the localization and interactions of native proteins than the relatively large protein fragments used in other methods; 2) the signal reaction being a simple reaction between a pair of protein-thiols and a thiol-selective small molecule fluorogen, it is less sensitive to the effects of variation of cellular conditions than the folding of fluorescent protein applications; 3) the inherent flexibility of the method of the present disclosure to design fluorogenic probes with many different spectral qualities that react specifically with different protein targets provides for the encoding of protein interactions in a variety of ways, including the potential for multiplexed protein expression analysis in vivo and in vitro; 4) fluorogenic labelling agents and methods are not limited in their application to a single assay, but are capable of being used in a series of assays in which the fluorogen and protein target sequence may be chosen according to their efficacy in a particular cell type appropriate to the study of the interactions of a given class of proteins; 5) methods of the disclosure can be automated and tailored for high-throughput fluorescent screening; and 6) markers are designed at the level of the atomic structure and three-dimensional conformation of the target protein motifs, allowing control over the flexibility and specificity of probe fragments (i.e., sulfhydryl tags) used.

"BODIPY derivative" is intended to encompass any chemically stable derivative of BODIPY that is fluorogenic and suitable for linking to a dimaleimide moiety, as well as BODIPY itself (also known as 4,4-difluoro-4-bora-3a,4a-diaza-s-indacene, or boron-dipyrromethene). Many BODIPY derivatives are known in the art, such as but not limited to BODIPY FL, BODIPY R6G, BODIPY TMR, BODIPY 581/591, BODIPY TR, BODIPY 630/650, and BODIPY 650/655, etc. These BODIPY derivatives are named for exemplary purposes only and are not meant to limit the compounds of the invention, as other fluorescent BODIPY derivatives can be used in fluorogenic labelling agents of the invention.

"Dimaleimide moiety" is intended to encompass a dimaleimide reactive unit capable of linking to a BODIPY derivative. It will be appreciated by the skilled artisan that many derivatives of a dimaleimide moiety exist or can be made. Such derivatives retaining ability to link to a fluorogenic BODIPY derivative and provide efficient quenching are intended to be encompassed by the present invention.

A dimaleimide moiety may be asymmetric or symmetric. An "asymmetric" dimaleimide moiety is one wherein the intrinsic reactivity of one maleimide is reduced, such that its intermolecular reaction is suppressed. A non-limiting example of an asymmetric dimaleimide moiety is the following:

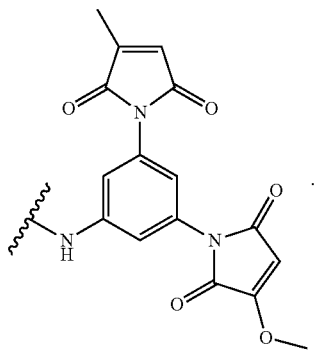 [SMILES: *Nc1cc(N2C(=O)C=C(C)C2=O)cc(N2C(=O)C=C(OC)C2=O)c1]

A non-limiting example of a symmetric dimaleimide moiety is the following:

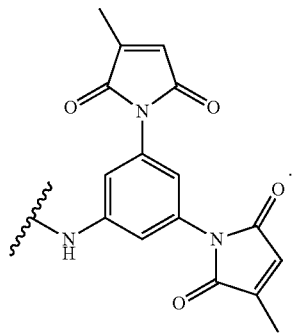 [SMILES: *Nc1cc(N2C(=O)C=C(C)C2=O)cc(N2C(=O)C=C(C)C2=O)c1]

In some embodiments, fluorogenic labelling agents provided herein comprise an asymmetric dimaleimide moiety. In other embodiments, fluorogenic labelling agents provided herein comprise a symmetric dimaleimide moiety.

It should be understood that a dimaleimide moiety may be covalently linked to a BODIPY derivative directly or via a linker. Many linker moieties are known in the art and may be used in compounds of the invention. In an embodiment, a linker is piperazine (diamide). Other non-limiting examples of linkers include sulfonamide, alkyne (e.g., acetylene linkage), triazole, urea, thiourea, and ketone. In another embodiment, a BODIPY derivative is linked directly to a dimaleimide moiety by a direct amide linkage with the common aryl on the dimaleimide moiety. In another embodiment, a BODIPY derivative is linked directly to a dimaleimide aryl moiety. In some embodiments, a BODIPY derivative is linked directly to a dimaleimide aryl moiety by a single bond, such as diarylamine, diarylether, and diarylthioether.

For compounds provided herein, it is intended that, in some embodiments, salts thereof are also encompassed. Those skilled in the art will appreciate that many salt forms (e.g., TFA salt, tetrazolium salt, sodium salt, potassium salt, etc,) are possible; appropriate salts are selected based on reaction and labelling conditions and other considerations known in the art. It is intended that suitable salts of the compounds presented herein are encompassed by the present invention.

In an embodiment, there is provided a fluorogenic labelling agent of Formula I, or a salt thereof:

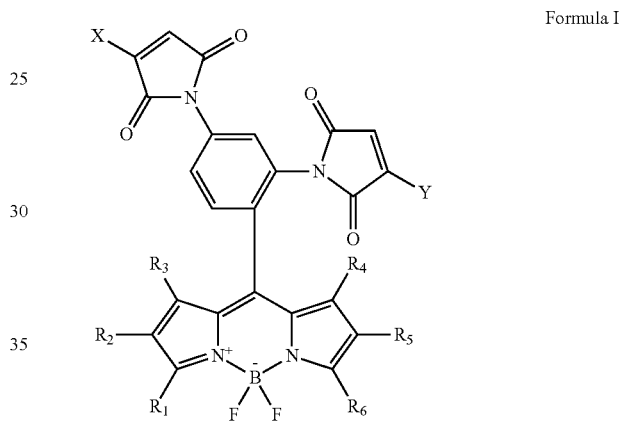

Formula I wherein:

$R_1$, $R_2$, $R_3$, $R_4$, $R_5$, and $R_6$ are independently selected from hydrogen, alkyl, alkenyl, alkynyl, cycloalkyl, cycloalkenyl, cycloalkynyl, aryl, alkaryl, arylalkyl, carboxy alkyl, aryl, heterocyclic, heteroaryl, and heteroaromatic, alkyl being optionally substituted by hydroxyl, amino, carboxyl, carboxylic ester, sulfonate, amide, carbamate, or aminoalkyl; and X and Y are independently $R_7$ or $OR_8$, wherein $R_7$ is selected from hydrogen, halogen, and alkyl, alkyl being optionally substituted by hydroxyl, amino, carboxyl, carboxylic ester, amide, carbamate, or aminoalkyl, and $R_8$ is alkyl, alkyl being optionally substituted by hydroxyl, amino, carboxyl, carboxylic ester, amide, carbamate, or aminoalkyl.

In some embodiments of fluorogenic labelling agents of Formula I, alkyl, alkenyl, alkynyl, cycloalkyl, cycloalkenyl, cycloalkynyl, aryl, alkaryl, arylalkyl, carboxy alkyl, aryl, heterocyclic, heteroaryl, or heteroaromatic are unsubstituted. In other embodiments of fluorogenic labelling agents of Formula I, alkyl, alkenyl, alkynyl, cycloalkyl, cycloalkenyl, cycloalkynyl, aryl, alkaryl, arylalkyl, carboxy alkyl, aryl, heterocyclic, heteroaryl, or heteroaromatic may be substituted by hydroxyl, amino, carboxyl, carboxylic ester, sulfonate, amide, carbamate, or aminoalkyl.

In an embodiment of fluorogenic labelling agents of Formula I, at least one of X and Y is $OR_8$. In another embodiment of fluorogenic labelling agents of Formula I, when one of X and Y is $OR_8$, then the other is $R_7$. In other words, in an embodiment of fluorogenic labelling agents of Formula I, when X is $OR_8$, Y is $R_7$. In another embodiment of fluorogenic labelling agents of Formula I, when Y is $OR_8$, X is $R_7$. In some embodiments of fluorogenic labelling agents of Formula I, X and Y are the same. In some embodiments of fluorogenic labelling agents of Formula I, $R_7$ and $R_8$ are the same. In some embodiments of fluorogenic labelling agents of Formula I, $R_7$ and $R_8$ are different.

In an embodiment of fluorogenic labelling agents of Formula I, X and Y are both $OR_8$. In an embodiment of fluorogenic labelling agents of Formula I, X and Y are both $OR_8$ where $R_8$ is alkyl. In an embodiment of fluorogenic labelling agents of Formula I, X and Y are both methoxy ($O-CH_3$).

In an embodiment of fluorogenic labelling agents of Formula I, $R_1$, $R_2$, $R_3$, $R_4$, $R_5$, and $R_6$ are the same. In an embodiment of fluorogenic labelling agents of Formula I, $R_1$, $R_2$, $R_3$, $R_4$, $R_5$, and $R_6$ are different. In an embodiment of fluorogenic labelling agents of Formula I, $R_2$ and $R_5$ are the same, and $R_1$, $R_3$, $R_4$, and $R_6$ are the same.

In an embodiment of fluorogenic labelling agents of Formula I, $R_1$, $R_2$, $R_3$, $R_4$, $R_5$, and $R_6$ are independently selected from hydrogen and alkyl. In an embodiment of fluorogenic labelling agents of Formula I, $R_2$ and $R_5$ are hydrogen and $R_1$, $R_3$, $R_4$, and $R_6$ are alkyl. In an embodiment of fluorogenic labelling agents of Formula I, $R_2$ and $R_5$ are hydrogen and $R_1$, $R_3$, $R_4$, and $R_6$ are methyl. In an embodiment of fluorogenic labelling agents of Formula I, $R_1$, $R_2$, $R_3$, $R_4$, $R_5$, and $R_6$ are hydrogen.

In an embodiment, there is provided a fluorogenic labelling agent of Formula II, or a salt thereof:

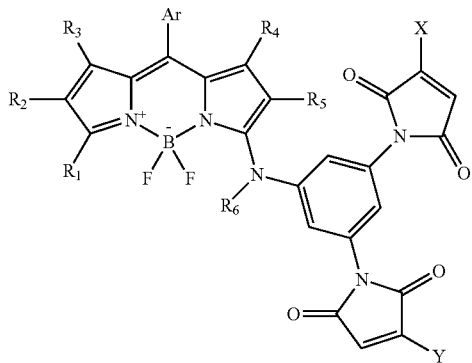

Formula II wherein:

$R_1$ is hydrogen, $R_1'$, $SR_1'$, $OR_1'$ or $NR_2'R_3'$, wherein $R_1'$, $R_2'$ and $R_3'$ are independently selected from hydrogen, alkyl, alkenyl, alkynyl, cycloalkyl, cycloalkenyl, cycloalkynyl, aryl, alkaryl, arylalkyl, and carboxy alkyl, alkyl being optionally substituted by hydroxyl, amino, carboxyl, carboxylic ester, sulfonate, amide, carbamate, or aminoalkyl; or $R_1'$ and $R_2$ or $R_1'$ and $R_3$ come together to form a 5, 6 or 7-membered ring which is selected from aryl, heterocyclic, heteroaryl, and heteroaromatic; or $R_2'$, $R_2$, $R_3'$, and $R_3$ come together independently to form at least one 5, 6 or 7-membered ring which is selected from aryl, heterocyclic, heteroaryl and heteroaromatic;

$R_2$, $R_3$, $R_4$, $R_5$ and $R_6$ are independently selected from hydrogen, alkyl, alkenyl, alkynyl, cycloalkyl, cycloalkenyl, cycloalkynyl, aryl, alkaryl, arylalkyl, carboxy alkyl, aryl, heterocyclic, heteroaryl, and heteroaromatic, alkyl being optionally substituted by hydroxyl, amino, carboxyl, carboxylic ester, sulfonate, amide, carbamate, or aminoalkyl;

X and Y are independently $R_7$ or $OR_8$, wherein $R_7$ is selected from hydrogen, halogen, and alkyl, alkyl being optionally substituted by hydroxyl, amino, carboxyl, carboxylic ester, amide, carbamate, or aminoalkyl, and $R_8$ is alkyl, alkyl being optionally substituted by hydroxyl, amino, carboxyl, carboxylic ester, amide, carbamate, or aminoalkyl; and Ar is aryl, heterocyclic, heteroaryl, or heteroaromatic and is optionally substituted by alkyl, cycloalkyl or halogen, alkyl being optionally substituted with hydroxyl, amino, carboxyl, sulfonate, carboxylic ester, amide, carbamate, or aminoalkyl.

In some embodiments of fluorogenic labelling agents of Formula II, alkyl, alkenyl, alkynyl, cycloalkyl, cycloalkenyl, cycloalkynyl, aryl, alkaryl, arylalkyl, carboxy alkyl, aryl, heterocyclic, heteroaryl, or heteroaromatic are unsubstituted. In other embodiments of fluorogenic labelling agents of Formula II, alkyl, alkenyl, alkynyl, cycloalkyl, cycloalkenyl, cycloalkynyl, aryl, alkaryl, arylalkyl, carboxy alkyl, aryl, heterocyclic, heteroaryl, or heteroaromatic may be substituted by hydroxyl, amino, carboxyl, carboxylic ester, sulfonate, amide, carbamate, or aminoalkyl.

In some embodiments of fluorogenic labelling agents of Formula II, Ar is phenyl, pyridine, pyrimidine or triazine and is optionally substituted by alkyl, cycloalkyl or halogen, alkyl being optionally substituted with hydroxyl, amino, carboxyl, sulfonate, carboxylic ester, amide, carbamate, or aminoalkyl.

In an embodiment of fluorogenic labelling agents of Formula II, at least one of X and Y is $OR_8$. In another embodiment of fluorogenic labelling agents of Formula II, when one of X and Y is $OR_8$, then the other is $R_7$. In other words, in an embodiment of fluorogenic labelling agents of Formula II, when X is $OR_8$, Y is $R_7$. In another embodiment of fluorogenic labelling agents of Formula II, when Y is $OR_8$, X is $R_7$. In some embodiments of fluorogenic labelling agents of Formula II, X and Y are the same. In some embodiments of fluorogenic labelling agents of Formula II, X and Y are different. In some embodiments of fluorogenic labelling agents of Formula II, $R_7$ and $R_8$ are the same. In some embodiments of fluorogenic labelling agents of Formula II, $R_7$ and $R_8$ are different.

In an embodiment of fluorogenic labelling agents of Formula II, X and Y are both $OR_8$. In an embodiment of fluorogenic labelling agents of Formula II, X and Y are both $OR_8$ where $R_8$ is alkyl. In an embodiment of fluorogenic labelling agents of Formula II, X and Y are both methoxy (also referred to as $O-CH_3$ or O-Me).

In an embodiment of fluorogenic labelling agents of Formula II, $R_2$, $R_3$, $R_4$, and $R_5$ are the same. In an embodiment of fluorogenic labelling agents of Formula II, $R_2$, $R_3$, $R_4$, and $R_5$ are different. In an embodiment of fluorogenic labelling agents of Formula II, $R_2$, $R_3$, $R_4$, $R_5$ and $R_6$ are the same. In an embodiment of fluorogenic labelling agents of Formula II, $R_2$, $R_3$, $R_4$, $R_5$ and $R_6$ are different. In an embodiment of fluorogenic labelling agents of Formula II, $R_2$, $R_3$, $R_4$, $R_5$, and $R_6$ are hydrogen.

In an embodiment of fluorogenic labelling agents of Formula II, $R_1$, $R_2$, $R_3$, $R_4$, $R_5$, and $R_6$ are hydrogen.

In some embodiments of fluorogenic labelling agents of Formula II, $R_1$ is an amino substituent, an oxygen substituent, a sulfur substituent, a thiol ether, or an ester.

In some embodiments of fluorogenic labelling agents of Formula II, $R_1$ is hydrogen. In some embodiments of fluorogenic labelling agents of Formula II, $R_1$ is $MeO_2CCH_2S$. In some embodiments of fluorogenic labelling agents of Formula II, $R_1$ is NMePh.

In an embodiment of fluorogenic labelling agents of Formula II, $R_1$ is $SR_1'$, $OR_1'$ or $NR_2'R_3'$ as defined above, and $R_2$, $R_3$, $R_4$, $R_5$ and $R_6$ are hydrogen.

In an embodiment, there is provided a fluorogenic labelling agent which is at least one of the compounds selected from YC23, YC28, and YC29, or a salt thereof.

In another broad aspect, there are provided herein methods of labelling and/or detecting specific protein targets, using fluorogenic compounds provided herein. In one embodiment, methods for labelling and/or detecting a target protein are provided, comprising contacting the target protein with a fluorogenic labelling agent of the invention, under conditions where the fluorogenic labelling agent reacts with sterically unhindered sulfhydryl groups on the target protein, and detecting a fluorescent signal from the fluorescent labelling agent, wherein the fluorescence of the fluorogenic labelling agent is quenched in the absence of reaction with the target protein, and detection of the fluorescent signal indicates that reaction of the fluorogenic labelling agent with the target protein has occurred. In some embodiments, the fluorescence of the fluorogenic labelling agent is quenched before reaction with a target protein, such that fluorescence is only detected after the fluorogenic labelling agent has reacted with the target protein, so that detection of fluorescence indicates that reaction has occurred and indicates presence of the target protein. In some embodiments, some fluorescence may be detected before the fluorogenic labelling agent has reacted with the target protein (e.g., before labelling), and fluorescence increases after the fluorogenic labelling agent has reacted with the target protein, such that an increase in fluorescence indicates that reaction has occurred, thereby indicating presence of the target protein.

Fluorogenic labelling agents may be used to fluorescently label and/or detect specific protein targets in vitro, in vivo, or ex vivo. In some embodiments, fluorogenic labelling agents are used in living cells for "live imaging," allowing visualization of a target protein's expression, localization, trafficking, and/or interactions inside a cell, or inside a living organism. Fluorogenic labelling agents and methods of use thereof may therefore provide valuable information about the function of target proteins that cannot be uncovered in vitro. Thus in some embodiments, reaction of a fluorogenic labelling agent and a target protein occurs in a living cell. A living cell may be a cultured cell, of which many types are known (e.g., a primary culture, a cell line, a transformed cell line, etc.). A living cell may be present in an organism, such as a transgenic animal, etc.

In some embodiments, a cell, e.g., a living cell, is an animal cell. Non-limiting examples of animal cells include mammalian cells, invertebrate cells, vertebrate cells, human cells, rodent cells, mouse cells, rat cells, insect cells, nematode cells, and fish cells.

In some embodiments, a fluorogenic labelling agent is not toxic to cells, e.g., is not toxic to animal cells.

In some embodiments of methods provided herein, a target protein is an intracellular protein. In some embodiments, a target protein is an extracellular or cell-surface protein. It will be understood that a fluorogenic labelling agent may react with, or label, a target protein intracellularly or extracellularly, depending on where the target protein is localized. In some embodiments, characteristics of the fluorogenic labelling agent are sufficient to allow intracellular labelling. For example, the fluorogenic labelling agent may have one or more of the following characteristics: selectivity/high specificity for the target protein; lack of background reactivity (e.g., lack of reaction with cellular proteins or glutathione); and efficient quenching of fluorescence before reaction with the target protein, coupled with bright fluorescence after reaction with the target protein. In the context of background reactivity, "lack of reaction with cellular proteins" is meant to refer to lack of fluorescent labeling reaction with native cellular proteins that are not linked, e.g., genetically fused, to a short peptide sequence or tag having two sterically unhindered sulfhydryl groups, e.g., Cys residues, separated by a corresponding distance.

In some embodiments, a target protein comprises a short peptide sequence having two sterically unhindered sulfhydryl groups, e.g., two Cysteine (Cys) residues, separated by an appropriate distance for reaction with a fluorogenic labelling agent of the invention. In one embodiment, the distance between the two sulfhydryl groups or Cys residues is about 10 Å. In an embodiment, a target protein comprises a dC10α tag. It should be understood that other tags may be used, as long as a tag includes two sulfhydryl groups separated by a corresponding distance, and reacts efficiently and appropriately to a fluorescent labelling agent, such that quenching of fluorescence is removed upon binding of the agent.

Generally, in methods provided herein, a target protein has been engineered to include a short peptide sequence or tag having two sterically unhindered sulfhydryl groups, e.g., Cys residues, separated by a corresponding distance. For methods conducted in vitro, for example, such a target protein may be synthesized in vitro or may be purified from a cell genetically engineered to express the target protein comprising the peptide sequence or tag. For methods conducted in vivo or ex vivo, in some embodiments a cell or organism may be genetically engineered to express the target protein comprising the peptide sequence or tag. Many such methods are known in the art.

In some embodiments, agents and methods provided herein are particularly advantageous for live imaging, due to the small size of the peptide sequence or tag linked to the target protein. In some embodiments, the peptide sequence or tag on the target protein does not significantly alter the function or localization of the target protein.

Many methods for detecting fluorescence are known and may be used in methods provided herein. Non-limiting examples of techniques used to detect fluorescence include fluorescence microscopy (e.g., with a fluorescence microscope, a confocal microscope, a total internal reflection fluorescence microscope (TIRFM), etc.); fluorescence spectroscopy (e.g., with a filter fluorometer, a spectrofluorometer, etc.); fluorescence resonance energy transfer (FRET); plate readers (e.g., microplate readers); HPLC fluorescence detectors; and so on. One skilled in the art will select the appropriate method of detecting fluorescence in accordance with the particular application or target protein being studied.

In some embodiments, an agent or method provided herein may be used in conjunction with a second labelling agent to detect a second target protein, for example in a double labelling experiment to allow simultaneous detection or visualization of two different target proteins, or to assay biomolecular interactions between two target proteins. In such experiments, typically the second labelling agent fluoresces at a different wavelength from the first fluorescent labelling agent, so that the two fluorescent signals can be distinguished. For example, there are provided methods for assaying biomolecular interactions between a first target protein and a second target protein, wherein the first target protein and the second target protein are each linked to a peptide having two sterically unhindered sulfhydryl groups separated by an appropriate distance for binding to a first fluorogenic labelling agent and a second fluorogenic labelling agent, respectively; the first target protein and the second target protein are contacted with the first fluorogenic labelling agent and the second fluorogenic labelling agent, respectively; and fluorescence of the first fluorogenic labelling agent and the second fluorogenic labelling agent are detected. The first and second fluorogenic labelling agents may comprise two different fluorogens, permitting detection of their interaction through a FRET-based fluorescent assay, for example. It will be appreciated that in addition to protein-protein interactions, other molecular interactions, such as protein-small molecule, protein-nucleic acid and protein-carbohydrate interactions, may be detected using similar methods.

Similarly, in some embodiments, an agent or method provided herein may be used in a double labelling experiment to allow simultaneous detection or visualization of two different target proteins, or to assay biomolecular interactions between two target proteins, where the second target protein is intrinsically fluorescent, e.g., the second target protein has been genetically fused to a fluorescent protein.

In another broad aspect of the invention, there are provided kits for labelling and/or detecting a target protein comprising a fluorogenic labelling agent of the invention and instructions for use thereof. A kit may also include reagents, solvents, buffers, etc., required for carrying out the methods described herein. In some embodiments, a kit includes a peptide comprising a dC10α tag. In some embodiments, a kit includes a vector encoding a dC10α tag suitable for use in cloning or expressing a protein of interest comprising the dC10α tag. Kits for live imaging of target proteins and for assaying biomolecular interactions are also provided.

EXAMPLES

The present invention will be more readily understood by referring to the following examples, which are provided to illustrate the invention and are not to be construed as limiting the scope thereof in any manner.

Unless defined otherwise or the context clearly dictates otherwise, all technical and scientific terms used herein have the same meaning as commonly understood by one of ordinary skill in the art to which this invention belongs. It should be understood that any methods and materials similar or equivalent to those described herein can be used in the practice or testing of the invention. A list of abbreviations used herein is given in Table 1.

Example 1. Design, Synthesis and Characterization of BODIPY Dimaleimide Fluorogen that can be Excited with Green Light Maleimides typically quench fluorescence in their conjugated form by acting as an acceptor in the d-PeT mechanism (Chen, Y. et al., Can. J. Chem. 2015, 93, 389-398). Designing fluorogens based on this quenching mechanism therefore poses two distinct challenges. First, in order to thermodynamically favour the transfer of an electron from the fluorophore excited state to the LUMO of the maleimide, the former should be higher in energy than the latter. Since the smaller band gaps of longer wavelength fluorophores are typically associated with lower energy excited states, it is more difficult for a given maleimide group to quench such a fluorophore. Second, the distance between the fluorophore excited state (ES) and the maleimide LUMO must be minimised in order to optimise quench efficiency. Indeed, it has been shown that ortho-substituted BODIPY derivatives bearing one maleimide group are more quenched than other derivatives, whose maleimide groups are more distant from the BODIPY excited state (Matsumoto, T. et al., Org. Lett. 2007, 9, 3375-3377).

We designed our novel fluorogens using a BODIPY skeleton and bearing two methoxymaleimide groups, at both the ortho position and the para position of the meso-phenyl ring (YC23; see FIG. 1A). As reported herein, these fluorogens were found to possess good quenching efficiency while maintaining high selectivity for reaction with a dithiol. DFT calculations were used to determine the energy levels of the frontier molecular orbitals involved in quenching and the labelling reaction. Molecular modelling using TD-DFT calculations confirmed that the distance between the ortho-maleimide and the BODIPY fluorophore excited state is short (FIG. 1A). Thus, we found that the ES was still higher than the maleimide-localised LUMO in the BODIPY-based fluorogens, even in BODIPY derivatives with small band gaps (long wavelength).

BODIPY fluorogen YC23 was synthesized as described below. Briefly, the meso-(2,4-dinitrophenyl) BODIPY intermediate was prepared by the condensation of 2,4-dinitrobenzaldehyde with 2,4-dimethylpyrrole. The nitro groups were then reduced by hydrogenation over palladium and the resulting amino groups were allowed to react with methoxymaleic anhydride. More details about compound synthesis are given below.

Figure 10:
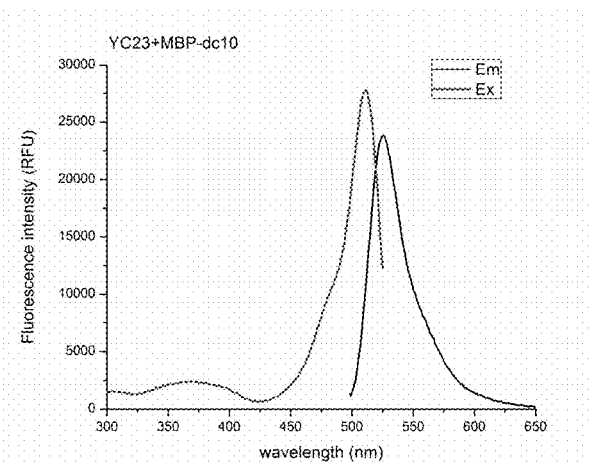
FIG. 10 shows excitation and emission spectra of 25 μM YC23-labelled MBP-dC10α (red: emission spectra; black: excitation spectra).

Maltose-binding protein (MBP) was chosen as a highly soluble test protein and the dC10α tag was fused to its C-terminus, as described previously, to give MBP-dC10α (Guy, J. et al., Mol. Biosyst. 2010, 6, 976-987). Fluorogen YC23 showed negligible background fluorescence (FIG. 1B, black line on x-axis), thus indicating that even with a methoxymaleimide group, whose LUMO is of slightly higher energy, quenching can still be very efficient, as long as one of the maleimide groups is in the ortho position. Subsequently, strong fluorescence was restored after reaction with our test protein MBP-dC10α, resulting in ca. 800-fold fluorescence enhancement at the emission maximum. Furthermore, the fluorescence increase was found to be concentration-dependent (FIG. 1B) and the excitation and emission maxima ($\lambda_{ex}$=510 nm, $\lambda_{em}$=525 nm; FIG. 10) were similar to those of the parent meso-phenyl BODIPY fluorophore (Matsumoto, T. et al., Org. Lett. 2007, 9, 3375-3377; Kollmannsberger, M. et al., J. Phys. Chem. A 1998, 102, 10211-10220).

The selectivity of fluorogen YC23 was tested by incubating it overnight in the presence of MBP-dC10α or other intracellular thiols. As shown in FIG. 1C, fluorescence was strongly restored upon reaction of 25 μM YC23 with 25 μM MBP-dC10α whereas much lower fluorescence (<10%) was observed after incubation with other thiols, even at the higher concentrations chosen to mimic the intracellular environment (250 μM Cys and Hcy, 1 mM GSH). Further kinetic studies of the reaction of YC23 with test protein MBP-dC10α revealed that although more than 4 hours were required to approach maximum fluorescence, after only 15 min a 10-fold increase was observed, which was sufficient to provide good contrast for cellular imaging.

Figure 2:
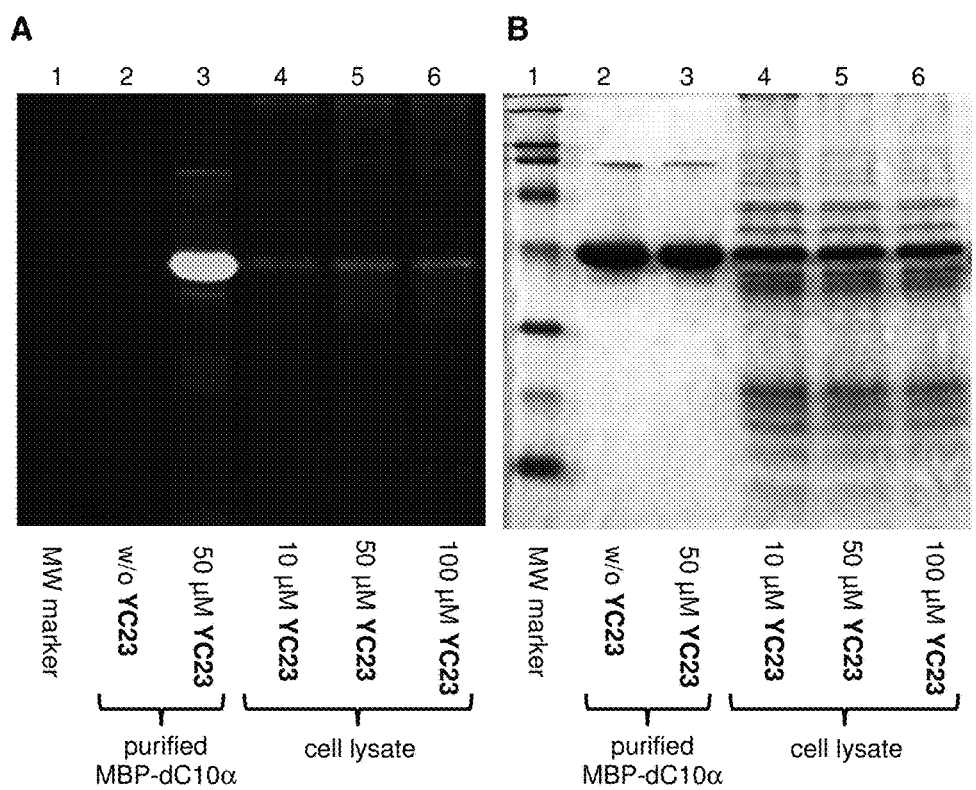
FIG. 2 shows that YC23 can selectively and robustly label test protein MBP-dC10α. 10% SDS-PAGE gels developed by (A) fluorescence ($\lambda_{ex}$=491 nm, $\lambda_{em}$=508 nm) and (B) Coomassie staining are shown. Lane 1: molecular weight markers. Lanes 2-3: Purified MBP-dC10α, concentrated to 50 μM and (lane 3) labelled with 50 μM YC23, prior to 10-fold dilution and loading. Lanes 4-6: Soluble lysate of bacteria expressing MBP-dC10α, treated with 10, 50, or 100 μM YC23 respectively and 0.5 mM TCEP overnight, prior to loading.

The thiol addition reaction of a maleimide group typically results in the formation of robust covalent bonds, which should be stable under conditions in which the labelled protein may itself undergo denaturation. To test this hypothesis, we expressed MBP-dC10α in *Escherichia coli* and used YC23 to label the test protein in bacterial lysate as well as the purified test protein. These samples were then heated to 95° C. for 15 min, prior to analysis by SDS-PAGE. As shown in lane 3 of FIG. 2A, the labelled purified test protein maintained its fluorescence even under these harsh denaturing conditions. Furthermore, as shown in lanes 4-6, as little as 10 µM of YC23 was sufficient to label the test protein, in the complex biological mixture of cell lysate. Comparison with the same lanes in the Coomassie-stained gel shown in FIG. 2B reveals the selectivity of the labelling process.

Figure 3:
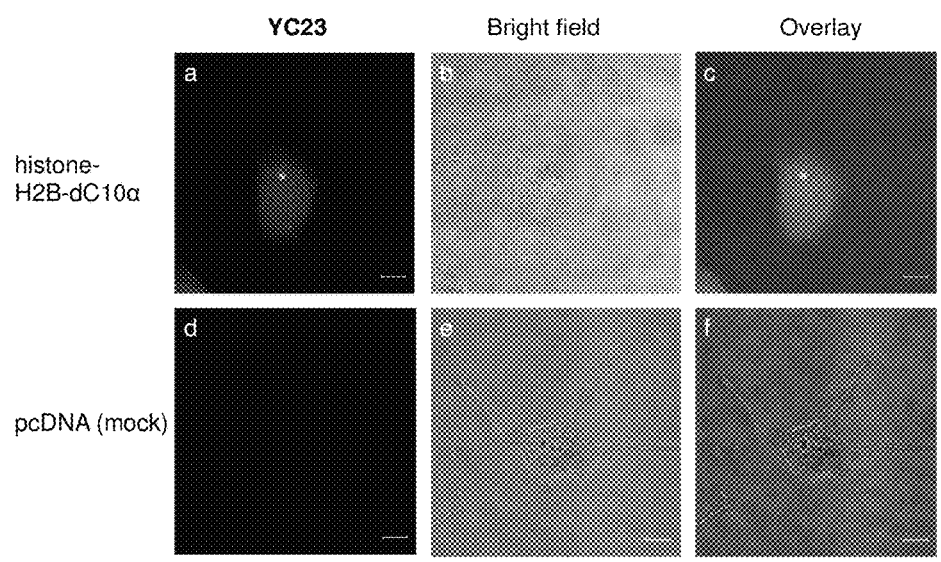
FIG. 3 shows fluorescence (left column), corresponding bright field (middle column) and the overlaid (right column) confocal microscopy images for cellular labelling with YC23. (A-C) show HEK293T cells expressing histone-H2B-dC10α treated with 10 μM YC23. (E-G) show pcDNA-transfected cells (negative control) treated with YC23. Scale bars=10 μm. Fluorescence imaging conditions: Laser: 488 nm, dichromic mirror: 488 nm, emission filter: 525/50 nm.
Figure 4:
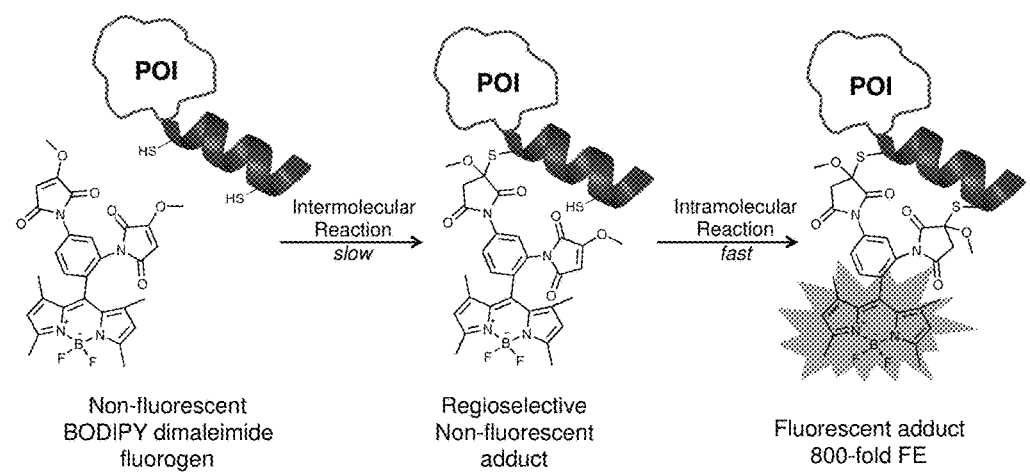
FIG. 4 shows a schematic diagram of protein labelling with a BODIPY dimaleimide fluorogen YC23, where a specific protein of interest (POI) is labelled with dimaleimide fluorogens.

Encouraged by this selectivity, we then tested whether YC23 could be used to label a target POI in mammalian cells. We first confirmed that incubation with up to 100 µM YC23 over 20 hours had a negligible effect on cell viability (FIG. 12a). For intracellular labelling, histone H2B was chosen as a test protein because it is well localized in the nucleus; the tag sequence dC10α was therefore cloned to the C-terminus of histone H2B, as described (Chen, Y. et al., Angew. Chem. Int. Ed., 2014, 53, 13785-13788). Human embryonic kidney (HEK293T) cells transfected with a plasmid encoding histone-H2B-dC10α were then incubated with 10 µM YC23 for 30 min; YC23 was removed and 15 min later the cells were imaged by fluorescence microscopy. As shown in FIG. 3, in cells transfected with histone-H2B-dC10α, the nuclei were strongly green fluorescent, indicating that YC23 specifically labelled histone-H2B-dC10α in these cells. Cells transfected with pcDNA (empty vector) as a negative control showed negligible fluorescence under the same conditions.

In summary, these experiments show that a novel protein-labelling fluorogen (YC23) based on a BODIPY fluorophore possessed latent green fluorescence that was efficiently quenched via a PeT mechanism with two proximal methoxymaleimide groups. The dimethoxymaleimide moiety conferred high selectivity for reaction with the dC10α tag, relative to other intracellular thiols. This green fluorogen could be used to label specific proteins in bacterial cell lysate and living mammalian cells, and this covalent labelling was robust enough to be compatible with routine SDS-PAGE, a facile and sensitive method for protein analysis.

Example 2. Design, Synthesis and Characterization of BODIPY Dimaleimide Fluorogen with Red Emission We designed complementary long-wavelength fluorogens that are visible in the red channel. As discussed above, the design of such a fluorogen posed a distinct photophysical challenge. Namely, the smaller band gap between the ground state (GS) and excited state (ES) of most long wavelength fluorophores is typically due to the low energy of the ES. However, as the relative energy of an ES of a given fluorophore decreases, the transfer of an electron from this ES to the LUMO of an adjacent maleimide group becomes less thermodynamically favoured, thereby decreasing quench efficiency. This means that for a red fluorophore to be well suited to PeT quenching by a maleimide group, having an ES higher in energy than the maleimide LUMO, the small band gap of that fluorophore must be due to the higher energy of its fluorophore GS.

First, we conceived a general synthetic strategy that would allow the introduction of substituents through subsequent $S_NAr$ reactions on a 3,5-dichloro-meso-phenyl BODIPY scaffold (shown in Scheme 1). The first chloride was displaced with 3,5-dinitroaniline, thereby incorporating the fragment to be transformed into the dimaleimide moiety. From this intermediate, the second chloride could be displaced with substituents that tune the colour of the latent fluorophore.

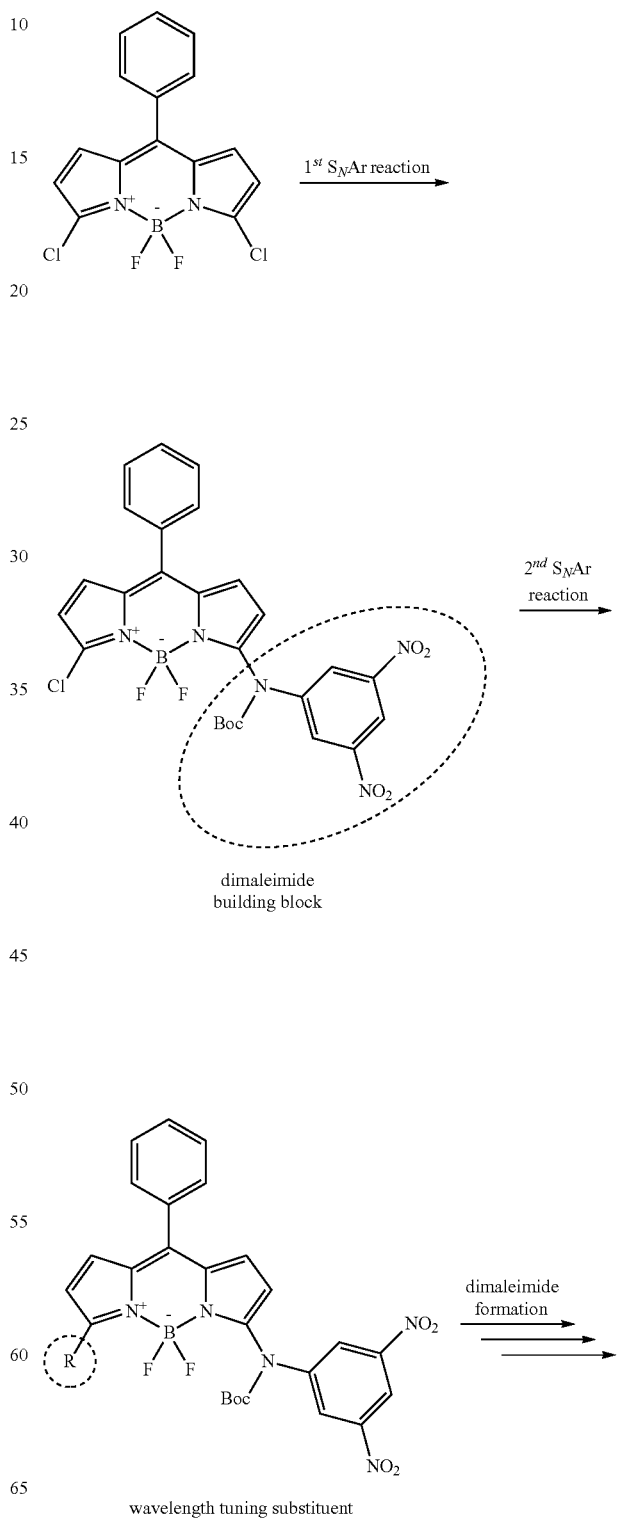

Scheme 1. General synthetic approach to tunable wavelength BODIPY fluorogens.

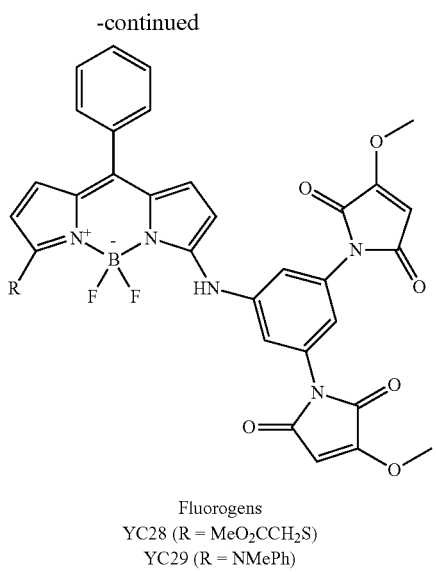

Fluorogens
YC28 (R = MeO$_2$CCH$_2$S)
YC29 (R = NMePh)

Figure 5:
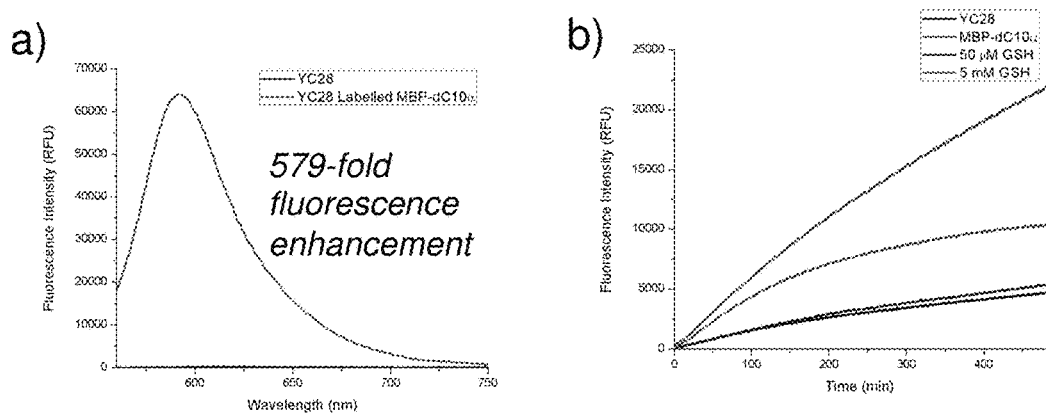
FIG. 5 shows characterization of the fluorogen YC28. (a) shows fluorescence enhancement ($\lambda_{ex}$=540 nm) of 25 μM fluorogen YC28, incubated in the absence (black) and presence of MBP-dC10α (red). (b) shows time-dependent fluorescence increase of 25 μM YC28 reacting with one equivalent of test protein MBP-dC10α (red) or two equivalents of tripeptide thiol GSH (blue), or with a large excess (40 eq) of GSH (green) or buffer only (black). $\lambda_{ex}$=540 nm, $\lambda_{em}$=590 nm.

First, we used methyl mercaptoacetate to displace the second chloride, giving fluorogen YC28 (synthesis is described in detail below). As shown in FIG. 5a, the fluorescence of YC28 was effectively quenched by the adjacent dimaleimide moiety, whereas the adduct formed upon reaction with the test protein MBP-dC10α was 579-fold more fluorescent. Furthermore, the emission spectrum of this adduct had a maximum at 592 nm. The kinetic selectivity of YC28 in its reaction with 25 µM MBP, relative to 5 mM glutathione (GSH, see FIG. 5b) was acceptable but not excellent. These results suggested that the thiol substituent on the BODIPY scaffold of YC28 may be itself labile to S$_N$Ar displacement in the presence of other thiols, or that the mono-thiolated adduct may show partly restored fluorescence. To investigate this further, we designed an even longer wavelength fluorogen, YC29, tuning orbital energies to maintain quench efficiency.

Figure 6:
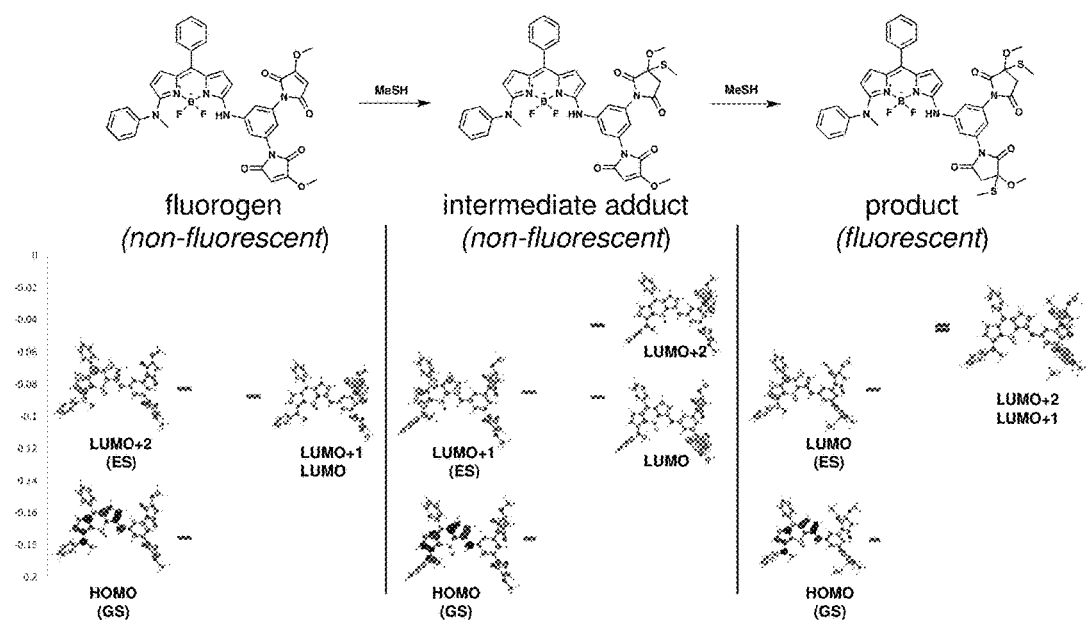
FIG. 6 shows the minimised structure and (frontier) molecular orbitals of the designed dimaleimide fluorogen YC29, its corresponding monosuccinimide thiol addition product and its final disuccinimide thiol addition product. Energy levels (in Hartree units) were calculated by Density Functional Theory (DFT) performed using Gaussian 09 at the B3LYP/6-31G(d) level of theory.
Figure 9:
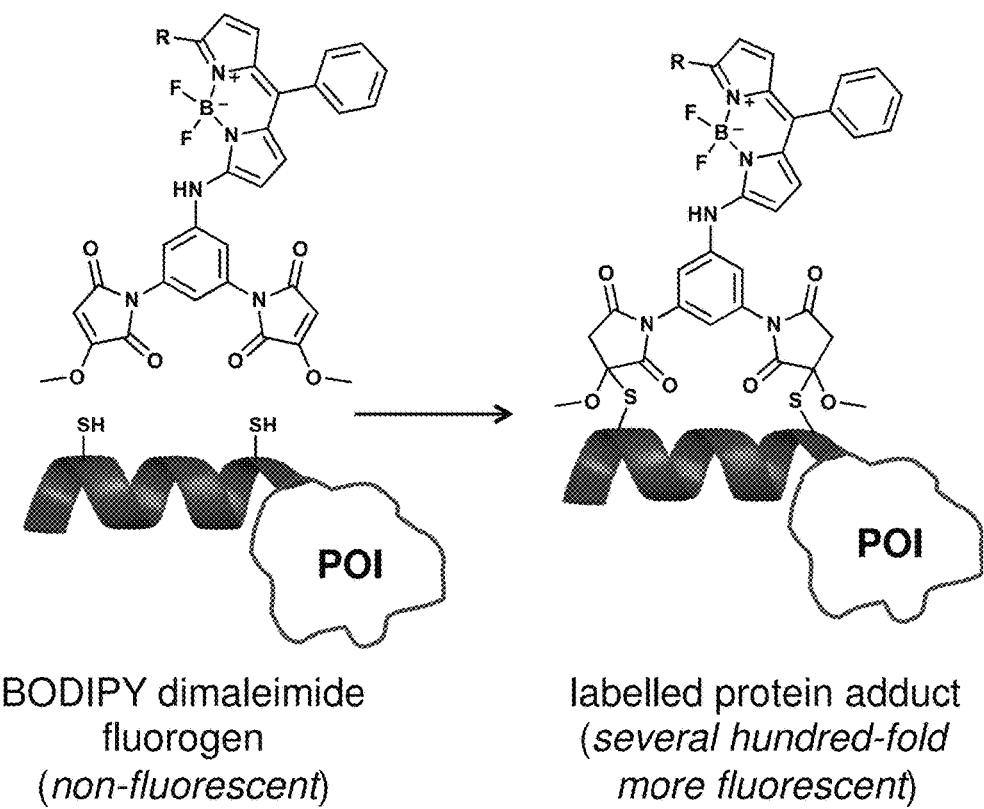
FIG. 9 shows a schematic diagram of protein labelling with a BODIPY dimaleimide fluorogen of Formula II, where a specific protein of interest (POI) is labelled by FlARe labelling with dimaleimide fluorogens.

More specifically, we designed fluorogens in silico and used DFT to calculate the energy levels of their relevant orbitals. Particular attention was paid to maintaining a small GS/ES band gap, in order to design a long wavelength fluorogen, while considering the relative energies of the ES and maleimide LUMO orbitals, in order to ensure quench efficiency in the fluorogen. We designed YC29 (R=NMePH, FIG. 9) to meet these design criteria. As shown in FIG. 6, although the narrow GS/ES band gap suggested the fluorescent emission should be red, the ES was still sufficiently high in energy to make electron transfer to the pendant methoxymaleimide group (LUMO) thermodynamically favourable.

Figure 7:
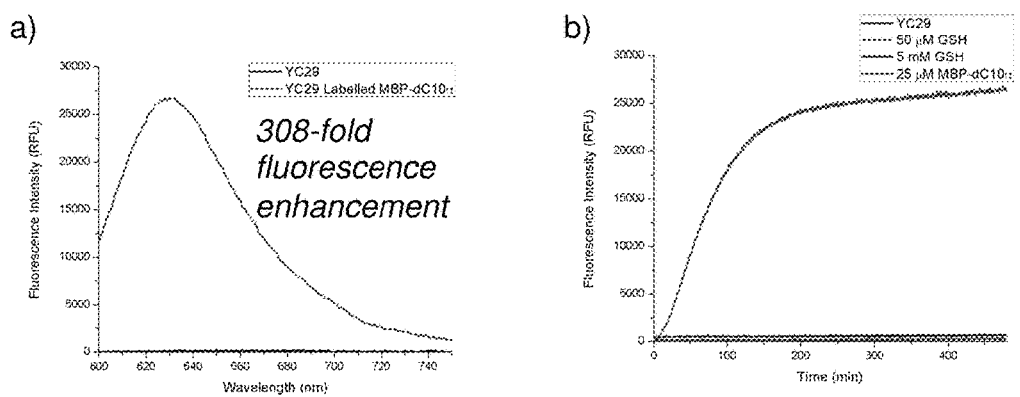
FIG. 7 shows characterization of the fluorogen YC29. (a) shows fluorescence enhancement ($\lambda_{ex}$=580 nm) of 25 μM fluorogen YC29, incubated in the absence (black) and presence of MBP-dC10α (red). (b) shows time-dependent fluorescence increase of 25 μM YC29 reacting with one equivalent of test protein MBP-dC10α (red), two equivalents of tripeptide thiol GSH (blue), with a large excess (40 eq) of GSH (green) or buffer only (black). $\lambda_{ex}$=580 nm, $\lambda_{em}$=630 nm.

YC29 was prepared according to a similar synthetic route as for YC28 (described in detail below). More details on compound synthesis are provided below. As is evident in FIG. 7a, the latent fluorescence of YC29 was also efficiently quenched, leading to a 308-fold fluorescence enhancement after reaction with the test protein MBP-dC10α. Moreover, the maximum of the emission spectrum was at 630 nm, placing it squarely in the red channel of most fluorescent microscopes. Furthermore, YC29 displayed excellent stability and selectivity. As shown in FIG. 7b, YC29 did not show any detectable reaction with 5 mM GSH, but reacted readily with 25 µM of the MBP-dC10α test protein. These results suggested suitability of YC29 for use as a selective intracellular protein labelling agent.

Figure 8:
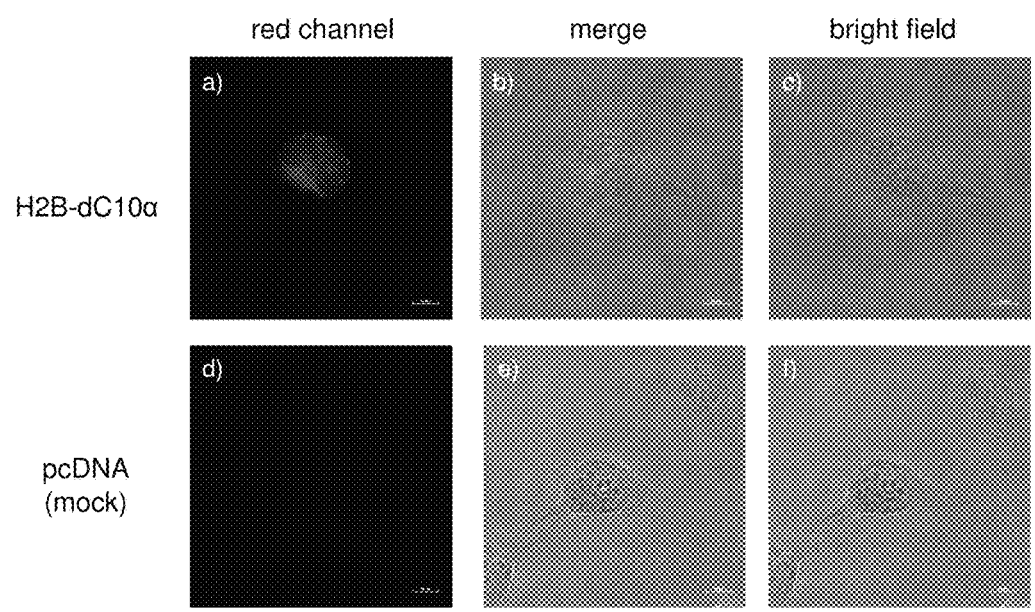
FIG. 8 shows fluorescence (left column), overlaid (middle column) and corresponding bright field (right column) confocal microscopy images for cellular labelling with YC29. (a-c) show HEK293T cells expressing histone-H2B-dC10α treated for 45 min with 10 μM YC29. (d-f) show pcDNA-transfected cells (negative control) treated with 10 μM YC29. Scale bars=10 μm. Fluorescence imaging conditions: Laser: 561 nm, dichromic mirror: 561 nm, emission filter: 595/50 nm.

Next, we evaluated YC29 in living cells. Briefly, the dC10α sequence was cloned to the C-terminus of histone H2B and HEK293T cells were transfected with the resulting expression plasmid, as described previously (Chen, Y. et al., Angew. Chem. Int. Ed. Engl. 2014). These cells were then labelled for 45 min with 10 µM YC29 prior to imaging. Intense red fluorescence was detected in cells expressing the histone H2B-dC10α target protein (FIG. 8a) and this fluorescence was localized in the nucleus (FIG. 8b), as expected for histone. In contrast, no red fluorescence was detected in cells transfected with mock DNA (FIG. 8d), attesting to the negligible background fluorescence and high selectivity of YC29.

In summary, these experiments showed that the considerable photophysical challenge of designing a red, PeT-based fluorogenic labelling agent was overcome. We have demonstrated that the BODIPY scaffold offered a versatile platform for controlling predicted colour and quench efficiency. Furthermore, S$_N$Ar reactions allowed the preparation of candidate labelling agents. YC29 in particular proved to be stable and highly selective, suitable for the intracellular labelling of a target protein in living cells.

Materials and Methods

1. General Procedures.

All reagents and solvents for reactions were used as received unless otherwise stated. Dichloromethane, methanol and tetrahydrofuran were dried with a solvent purification system from LC Technology Solution Inc. (Salisbury, Mass., USA). All reactions were performed under an inert atmosphere (e.g., N$_2$) in oven-dried apparatus unless otherwise stated.

Reactions were monitored by thin layer chromatography (TLC) using E. Merck silica gel 60F$_{254}$ pre-coated aluminium plates. Components were visualized by illumination with a short-wavelength ultra-violet light or long-wavelength visible light after which staining in KMnO$_4$ solution followed by heating. Flash column chromatography was performed on ZEOCHEM® silica gel 60 (ECO 40-63 µm) using ethyl acetate/n-hexane or acetonitrile/dichloromethane as eluting solvents.

Nuclear magnetic resonance (NMR) spectra were recorded at ambient temperature in deuterochloroform with tetramethylsilane (TMS) as internal reference unless otherwise stated. The experiments were performed mainly on a Bruker Avance 400 Fourier Transform Spectrometer operating at 400 MHz for $^1$H and at 100.6 MHz for $^{13}$C.

EI-MS spectra were recorded on a Kratos Concept mass spectrometer for both low resolution and high resolution mass spectra. ESI-MS spectra were recorded on a Waters Micromass Q-Tof mass spectrometer.

Melting points were measured on an EZ-Melt automated melting point apparatus and uncorrected.

Ultraviolet absorption spectra and fluorescence spectroscopic studies were performed on a Synergy H4 Hybrid Multi-Mode Microplate Reader.

2. Cloning and Expression.

Cloning of histone-H2B-dC10α and cloning and expression of test protein MBP-dC10α followed previously published protocols (Chen, Y. et al., Angew. Chem. Int. Ed. Engl. 2014, 53, 13785-13788; Guy, J. et al., Mol. Biosyst. 2010, 6, 976-987).

3. Determination of Fluorescence Properties of Fluorogens, Fluorescence Changes after Labelling of Target Protein, Selectivity Over Other Thiols, and Fluorescence Enhancement Ratios.

Figure 11:
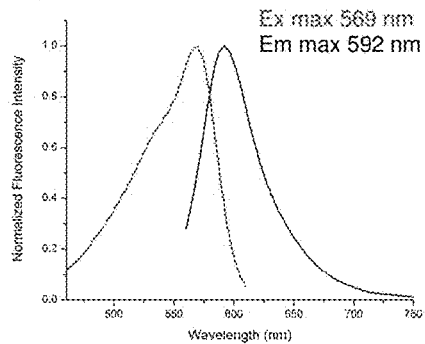
FIG. 11 shows excitation and emission spectra of 25 μM MBP-dC10α labelled with (a) YC28 (red: excitation spectra; black: emission spectra) or (b) YC29 (red: emission spectra; black: excitation spectra).
Figure 11:
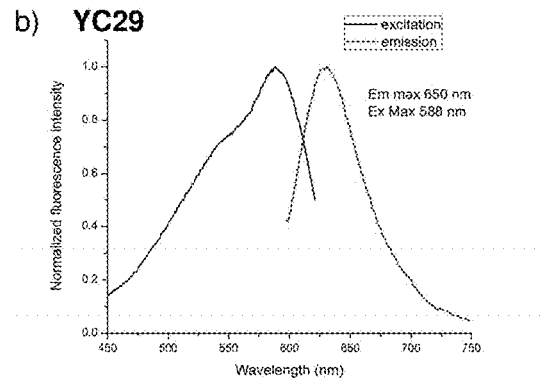

Emission spectra and fluorescence intensity measurements were recorded at 37° C. with a Synergy H4 Hybrid Multi-Mode Microplate Reader with excitation and emission monochromators set at 9 nm bandpass. Concentrations of 2.5, 5, 12.5, 20, and 25 µM of MBP-dC10α were reacted with 25 µM YC23. The mixture of 25 µM solution of YC23 and 2.5, 5, 12.5 20, or 25 µM MBP-dC10α in 50 mM HEPES buffer (pH 7.4) with 5% DMSO was incubated at 37° C. in the dark for overnight after which the fluorescence emission spectrum was recorded ($\lambda_{ex}$=480 nm). The emission spectra of YC23 in the same solution without MBP-dC10α were also recorded. The ratio of fluorescence intensity at maximum emission gave the fluorescence enhancement ratio. Selectivity tests were done with same protocol but with different concentrations of thiols. The mixture of 25 µM solution of YC28 or YC29 and 25 µM MBP-dC10α in 50 mM HEPES buffer (pH 7.4) with 5% DMSO was incubated at 37° C. in the dark for overnight after which the fluorescence emission spectrum was recorded. The emission spectra of YC28 or YC29 in the same solution without MBP-dC10α were also recorded. The ratio of fluorescence intensity at maximum emission gave the fluorescence enhancement ratio. $\lambda_{ex}$ for YC28 is 540 nm and $\lambda_{ex}$ for YC29 is 580 nm. Excitation and emission spectra were obtained for 25 µM of MBP-dC10α labelled with one equivalent of YC23 (FIG. 10), YC28 (FIG. 11a) or YC29 (FIG. 11b).

4. Time-Dependent Fluorescence Increase for Kinetic Studies.

Protein labelling kinetics were studied by following the time-dependent fluorescence increase at 37° C. using a Synergy H4 Hybrid Multi-Mode Microplate Reader with excitation and emission monochromators set at a 9-nm bandpass. The reaction was prepared in 50 mM HEPES buffer (pH 7.4) with 5% DMSO. Solutions of MBP-dC10α were prepared in a 96-well plate and labelling reagent YC23, YC28 or YC29 in DMSO was added immediately before recording. The final concentrations of YC23, YC28, YC29 and of MBP-dC10α were all 25 µM in 50 mM HEPES buffer (pH 7.4) with 5% DMSO. Samples were excited at 495 nm (YC23), 540 nm (YC28) or 580 nm (YC29) and fluorescence intensity was followed at 525 nm (YC23), 590 nm (YC28) or 630 nm (YC29) as a function of time.

5. Cellular Labelling.

HEK 293T cells were plated into 60-mm dishes and grown in MEM supplemented with 10% FBS, 100 units/mL of penicillin and 100 µg/mL of streptomycin for 16 h before transfection. Cells were transiently transfected with histone H2B-dC10α or pcDNA3.1 (mock) using lipofectamine 2000 following the manufacturer's instructions. Twenty-four hours after transfection, the cells were incubated with 10 µM YC23 or YC29 (in Opti-MEM with 0.2% DMSO) for 45 min at 37° C. Cells were observed and imaged on a Nikon confocal microscope with a 25× objective. Images were taken and analyzed with NIS-Elements software.

6. MTT Assay.

3-(4,5-Dimethylthiazol-2-yl)-2,5-diphenyl tetrazolium bromide (MTT) is a yellow tetrazolium salt and can be reduced to formazan crystals, which are insoluble in aqueous solutions, by active mitochondria in living cells. The resulting intracellular purple formazan can be dissolved in Triton X100, and therefore quantified by measuring absorption of the solution.

Figure 12:
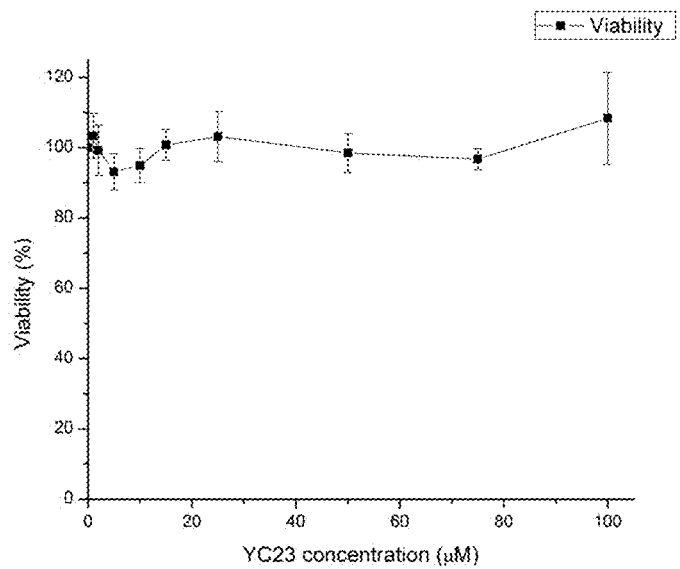
FIG. 12 shows cytotoxicity of (a) YC23 and (b) YC29 in cultured HEK293T cells. Cells were incubated with the corresponding concentrations of fluorogen for 20 h. Cell viability was measured by MTT assay and the results are reported as percentage relative to untreated cells (mean±SD).
Figure 12:
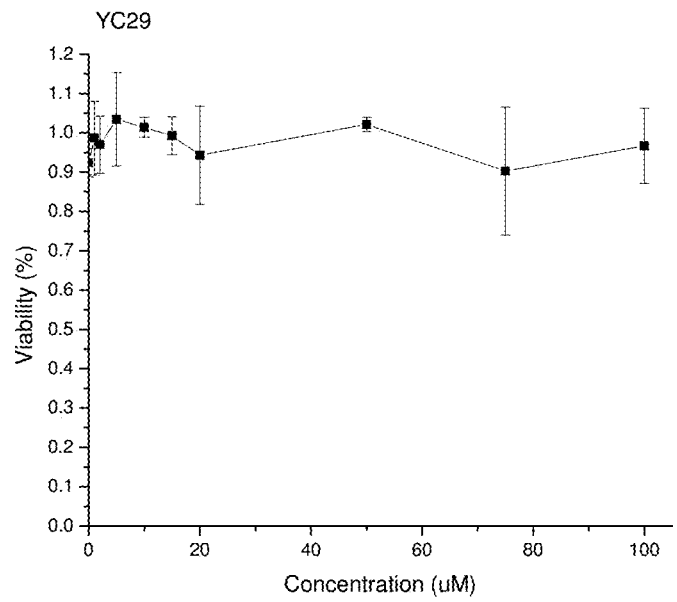

Cells were seeded in a 96-well plate and incubated with 100 µL of culture medium with different amounts of the fluorogen YCx for 20 h. No fluorogen was added to the positive control and no cells were plated in the negative control. Portions of 25 µL of MTT solution (5 mg in 1 mL of Hanks' balanced salt solution) were added to the wells and the cells were further incubated at 37° C. for 4 h. Solubilization solutions (100 µL) were then added and incubated in 96-well plates at room temperature in the dark overnight. The absorption of each well was measured using a plate reader at a wavelength of 570 nm with 690 nm as a reference. Cell viability was calculated according to the following equation:

Cell viability=$(A_{with\ fluorogen}-A_{negative\ control})/(A_{positive\ control}-A_{negative\ control})\times 100\%$ Cytotoxicity of YC23 (a) and YC29 (b) in cultured HEK293T cells is shown in FIG. 12.

Synthesis Methods and Characterization

Synthesis of YC23

The synthetic route for the preparation of fluorogen YC23 is shown in Scheme 2.

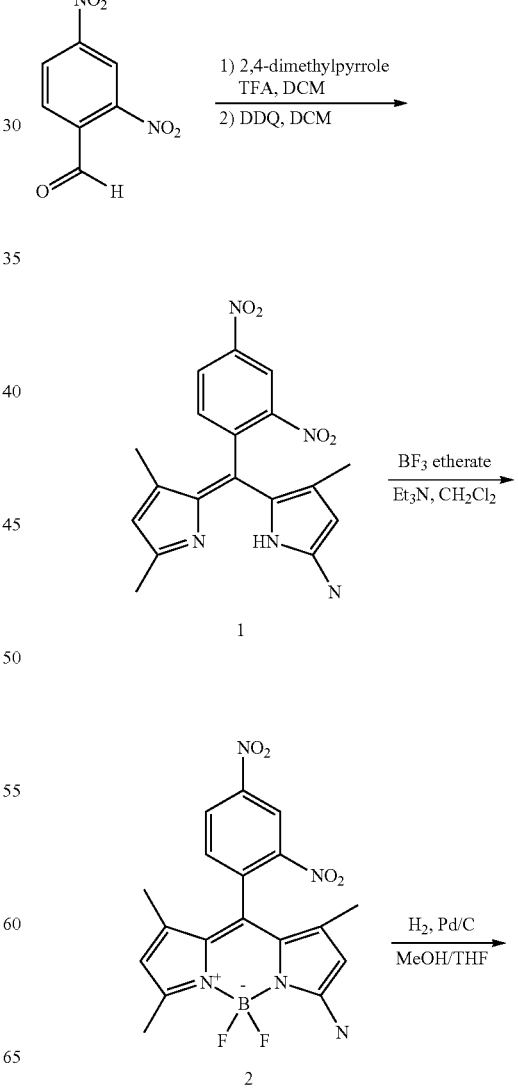

Scheme 2. Synthetic route for the preparation of fluorogen YC23.

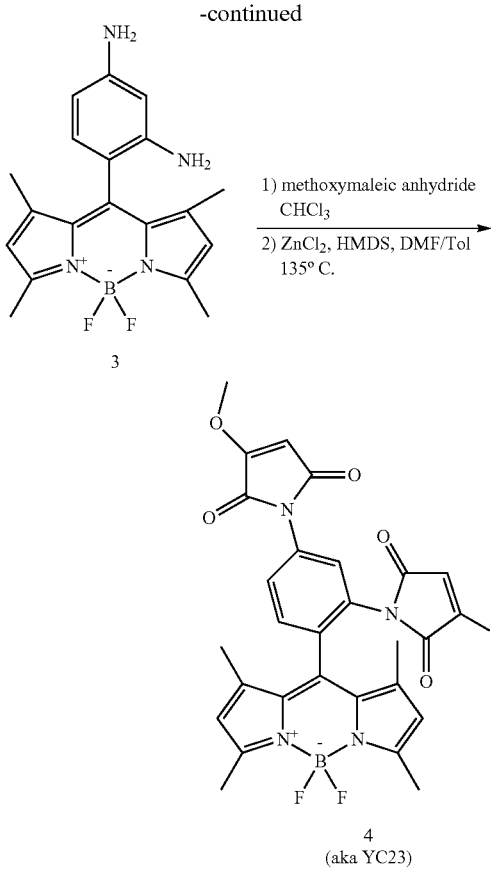

(Z)-2-((3,5-Dimethyl-2H-pyrrol-2-ylidene)(2,4-dinitrophenyl)methyl)-3,5-dimethyl-1H-pyrrole (1)

2,4-Dinitrobenzaldehyde (392 mg, 2.0 mmol) and 2,4-dimethylpyrrole (412 μL, 4.0 mmol) were dissolved in 50 mL of absolute $CH_2Cl_2$ under an $N_2$ atmosphere. A drop of TFA was added and the solution was stirred at room temperature overnight. When monitoring by TLC showed complete consumption of aldehyde, a solution of DDQ in $CH_2Cl_2$ was added and stirring was continued for 1 h. The reaction mixture was washed with water, dried over $Na_2SO_4$, filtered and evaporated to dryness. The crude intermediate was purified by a short column chromatography to give compound 1 as a brown solid (378 mg, 50% yield). $^1$H NMR (400 MHz, $CDCl_3$): δ (ppm) 8.88 (d, J=1.92 Hz, 1H), 8.51 (dd, J=8.44, 1.96 Hz, 1H), 7.70 (d, J=8.36 Hz, 1H), 5.89 (s, 2H), 2.32 (s, 6H), 1.27 (s, 6H); $^{13}$C NMR (100 MHz, $CDCl_3$): δ (ppm) 153.11, 149.72, 148.01, 139.47, 138.29, 134.08, 129.87, 127.18, 120.73, 11.98, 16.08, 14.32; LRMS (EI) m/z (%): 366.1 ($M^+$, 28%); HRMS (EI): calcd for $C_{19}H_{18}N_4O_4$: 366.1382, found: 366.1310.

10-(2,4-Dinitrophenyl)-5,5-difluoro-1,3,7,9-tetramethyl-5H-dipyrrolo[1,2-c:2',1'-f][1,3,2]diazaborinin-4-ium-5-uide (2)

Compound 1 (378 mg, 1.03 mmol) was dissolved in anhydrous $CH_2Cl_2$ and $Et_3N$ (2.8 mL, 20 mmol) was added under $N_2$. The reaction mixture was stirred and cooled to 0° C. in an ice bath. To the cooled solution, boron trifluoride etherate (2.8 mL, 22 mmol) was added dropwise and the solution was warmed to room temperature and stirred for another 1 h. The reaction mixture was then washed with $H_2O$, dried over $MgSO_4$, filtered and evaporated to dryness. The crude product obtained was purified by column chromatography to yield compound 2 as red crystals (123 mg, 29% yield). m.p. 216.9-218.6° C. $^1$H NMR (400 MHz, $CDCl_3$): δ (ppm) 8.95 (d, J=2.0 Hz, 1H), 8.59 (dd, J=8.36, 2.08 Hz, 1H), 7.69 (d, J=8.36 Hz, 1H), 6.00 (s, 2H), 2.52 (s, 6H), 1.33 (s, 6H); $^{13}$C NMR (100 MHz, $CDCl_3$): δ (ppm) 157.33, 148.85, 148.52, 141.31, 136.17, 133.06, 130.13, 128.01, 122.24, 120.31, 14.68, 14.11; LRMS (EI) m/z (%): 414.1 ($M^+$, 100%); HRMS (EI): calcd for $C_{19}H_{17}BF_2N_4O_4$: 414.1311, found: 414.1333.

10-(2,4-Diaminophenyl)-5,5-difluoro-1,3,7,9-tetramethyl-5H-dipyrrolo[1,2-c:2',1'-f][1,3,2]diazaborinin-4-ium-5-uide (3)

To a solution of compound 2 (120 mg, 0.29 mmol) in MeOH (3 mL)/THF (3 mL) was added Pd/C (6 mg, 5% m/m). The reaction mixture was stirred under $H_2$ at room temperature overnight. The reaction mixture was filtered through celite to remove Pd/C. The filtrate was then evaporated to dryness to give 57 mg (56% yield) of product 3, which was used directly in the next steps without further purification. LRMS (EI) m/z (%): 354.2 ($[M]^+$, 100%); HRMS (EI): calcd for $C_{19}H_{21}BF_2N_4$: 354.1827, found: 354.1831.

10-(2,4-Bis(3-methoxy-2,5-dioxo-2,5-dihydro-1H-pyrrol-1-yl)phenyl)-5,5-difluoro-1,3,7,9-tetramethyl-5H-dipyrrolo[1,2-c:2',1'-f][1,3,2]diazaborinin-4-ium-5-uide (4, aka YC23)

Methoxymaleic anhydride (36 mg, 0.28 mmol) was added to a solution of 3 (50 mg, 0.14 mmol) in $CHCl_3$ and the resulting mixture was stirred at 25° C. for 3 h, after which volatiles were evaporated under reduced pressure. The crude mixture was suspended in $Et_2O$ and filtered under reduced pressure, yielding the dimaleamic acid, which was used in the next step without further purification. The dimaleamic acid and $ZnCl_2$ (57 mg, 0.42 mmol) were dissolved in toluene-DMF (90:10) before a dilute solution of HMDS (132 μL) in toluene was added over 20 min. The resulting mixture was then heated to reflux for 2 h after which the volatiles were evaporated under reduced pressure. The resulting residue was dissolved in EtOAc and washed successively with 0.1 M HCl and saturated $Na_2CO_3$ (aq). The crude product was then purified by flash chromatography on silica gel giving compound 4 (aka YC23) (7.7 mg, 10% yield). $^1$H NMR (400 MHz, $CDCl_3$): δ (ppm) 7.76 (dd, J=8.4, 2.0 Hz, 1H), 7.58 (d, J=2.1 Hz, 1H), 7.49 (d, J=8.4 Hz, 1H), 5.94 (s, 2H), 5.60 (s, 1H), 5.36 (s, 1H), 4.01 (s, 3H), 3.88 (s, 3H), 2.49 (s, 6H), 1.58 (s, 6H); $^{13}$C NMR (100 MHz, $CDCl_3$): δ (ppm) 168.41, 168.08, 164.18, 163.56, 160.78, 160.29, 156.02, 143.95, 135.76, 133.49, 133.30, 131.24, 131.19, 130.78, 126.55, 125.50, 121.61, 96.87, 96.75, 59.28, 59.00, 14.87, 14.70; LRMS (ESI) m/z (%): 575.0 ($[M+H]^+$), 597.0 ($[M+Na]^+$); HRMS (ESI): calcd for $C_{29}H_{25}BF_2N_4NaO_6$: 595.1735, found: 597.1738.

Synthesis of YC28

The synthetic route for the preparation of fluorogen YC28 is shown in Scheme 3.

Scheme 3. Synthetic route for the preparation of Fluorogen YC28.

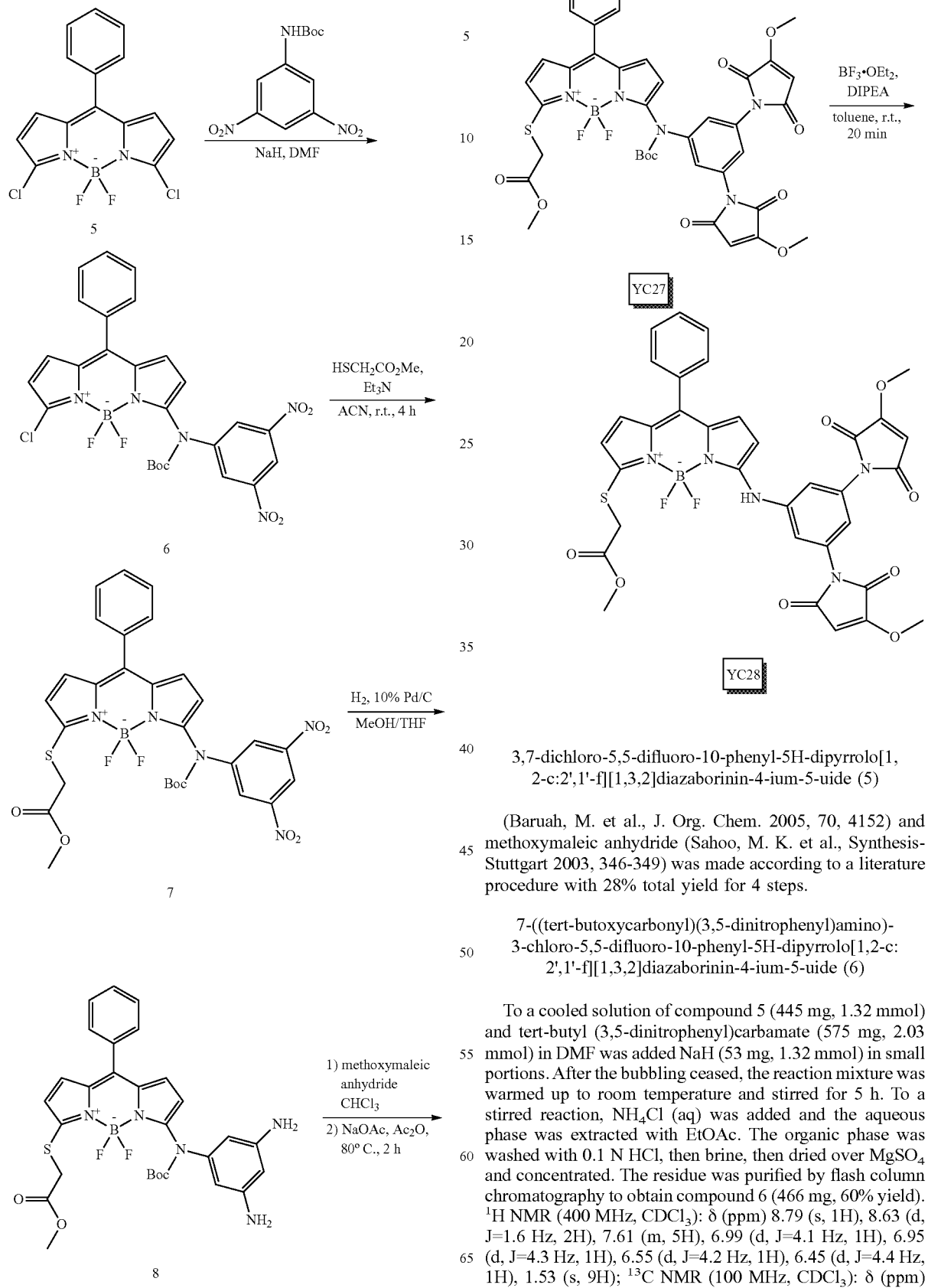

3,7-dichloro-5,5-difluoro-10-phenyl-5H-dipyrrolo[1,
2-c:2',1'-f][1,3,2]diazaborinin-4-ium-5-uide (5)

(Baruah, M. et al., J. Org. Chem. 2005, 70, 4152) and methoxymaleic anhydride (Sahoo, M. K. et al., Synthesis-Stuttgart 2003, 346-349) was made according to a literature procedure with 28% total yield for 4 steps.

7-((tert-butoxycarbonyl)(3,5-dinitrophenyl)amino)-
3-chloro-5,5-difluoro-10-phenyl-5H-dipyrrolo[1,2-c:
2',1'-f][1,3,2]diazaborinin-4-ium-5-uide (6)

To a cooled solution of compound 5 (445 mg, 1.32 mmol) and tert-butyl (3,5-dinitrophenyl)carbamate (575 mg, 2.03 mmol) in DMF was added NaH (53 mg, 1.32 mmol) in small portions. After the bubbling ceased, the reaction mixture was warmed up to room temperature and stirred for 5 h. To a stirred reaction, NH$_4$Cl (aq) was added and the aqueous phase was extracted with EtOAc. The organic phase was washed with 0.1 N HCl, then brine, then dried over MgSO$_4$ and concentrated. The residue was purified by flash column chromatography to obtain compound 6 (466 mg, 60% yield). $^1$H NMR (400 MHz, CDCl$_3$): δ (ppm) 8.79 (s, 1H), 8.63 (d, J=1.6 Hz, 2H), 7.61 (m, 5H), 6.99 (d, J=4.1 Hz, 1H), 6.95 (d, J=4.3 Hz, 1H), 6.55 (d, J=4.2 Hz, 1H), 6.45 (d, J=4.4 Hz, 1H), 1.53 (s, 9H); $^{13}$C NMR (100 MHz, CDCl$_3$): δ (ppm) 151.53, 148.23, 147.14, 146.24, 143.94, 134.57, 133.30, 132.34, 131.24, 130.82, 130.66, 128.70, 123.88, 119.98, 117.34, 114.56, 84.76, 27.97; $^{19}$F NMR (376.7 MHz, CDCl$_3$): δ (ppm) −146.82 (s); LRMS (ESI) m/z: 606.1 ([M+Na]$^+$); HRMS (ESI): calcd for C$_{26}$H$_{21}$BClF$_2$N$_5$NaO$_6$: 606.1144, found: 606.1135.

7-((tert-butoxycarbonyl)(3,5-dinitrophenyl)amino)-5, 5-difluoro-3-((2-methoxy-2-oxoethyl)thio)-10-phenyl-5H-dipyrrolo[1,2-c:2',1'-f][1,3,2]diazaborinin-4-ium-5-uide (7)

To a mixture of methyl 2-mercaptoacetate (179 μL, 2 mmol) and compound 6 (583 mg, 1 mmol) in anhydrous of acetonitrile was added Et$_3$N (139 μL, 1 mmol); the reaction mixture was stirred at room temperature for 4 h. The volatile components were evaporated under reduced pressure and the residue was purified by flash column chromatography to obtain compound 7 (615 mg, 94% yield). $^1$H NMR (400 MHz, CDCl$_3$): δ (ppm) 8.75 (t, J=2.0 Hz, 1H), 8.61 (d, J=2.0 Hz, 2H), 7.52 (m, 5H), 6.95 (d, J=4.6 Hz, 1H), 6.79 (d, J=3.9 Hz, 1H), 6.57 (d, J=4.6 Hz, 1H), 6.42 (d, J=4.0 Hz, 1H), 3.76 (s, 2H), 3.75 (s, 3H), 1.53 (s, 9H); $^{13}$C NMR (100 MHz, CDCl$_3$): δ (ppm) 168.19, 161.51, 151.89, 148.1833, 145.20, 144.35, 142.38, 137.41, 133.57, 132.98, 131.98, 130.66, 130.55, 128.55, 127.60, 123.75, 119.21, 115.74, 114.24, 84.32, 53.16, 34.18, 27.99; $^{19}$F NMR (376.7 MHz, CDCl$_3$): δ (ppm) −147.05 (s); LRMS (ESI) m/z (%): 676.8 ([M+Na]$^+$); HRMS (ESI): calcd for C$_{29}$H$_{26}$BF$_2$N$_5$NaO$_8$S: 676.1466, found: 676.1444.

7-((tert-butoxycarbonyl)(3,5-diaminophenyl)amino)-5,5-difluoro-3-((2-methoxy-2-oxoethyl)thio)-10-phenyl-5H-dipyrrolo[1,2-c:2',1'-f][1,3,2]diazaborinin-4-ium-5-uide (8)

Compound 7 (210 mg, 0.32 mmol) was dissolved in MeOH/THF (2 mL/2 mL) and the solution was purged with N$_2$ for 15 min. Pd/C (10 mg, 5% m/m) was then added to the solution, and the reaction mixture was stirred under H$_2$ overnight. The final reaction mixture was filtered through celite to remove Pd/C and the filtrate was evaporated to dryness. The residue was purified by a short flash column chromatography to obtain compound 8 (133 mg, 69% yield). $^1$H NMR (400 MHz, CDCl$_3$): δ (ppm) 7.46 (m, 7H), 6.78 (s, 1H), 6.69 (s, 1H), 6.48 (s, 1H), 6.22 (s, 3H), 5.82 (s, 1H), 3.78 (s, 2H), 3.72 (s, 3H), 3.28 (br, 4H), 1.44 (s, 9H); $^{13}$C NMR (100 MHz, CDCl$_3$): δ (ppm) 168.84, 156.61, 153.09, 151.76, 147.66, 142.99, 141.86, 136.41, 133.50, 132.10, 130.50, 130.19, 129.35, 128.34, 117.80, 116.50, 104.04, 100.09, 81.96, 53.00, 34.57, 28.11; $^{19}$F NMR (376.7 MHz, CDCl$_3$): δ (ppm) −145.16 (s); LRMS (ESI) m/z: 616.2 ([M+Na]$^+$); HRMS (ESI): calcd for C$_{29}$H$_{30}$BF$_2$N$_5$NaO$_4$S: 616.1982, found: 616.1989.

7-((3,5-bis(3-methoxy-2,5-dioxo-2,5-dihydro-1H-pyrrol-1-yl)phenyl)(tert-butoxycarbonyl)amino)-5,5-difluoro-3-((2-methoxy-2-oxoethyl)thio)-10-phenyl-5H-dipyrrolo[1,2-c:2',1'4][1,3,2]diazaborinin-4-ium-5-uide (YC27)

Methoxymaleic anhydride (243 mg, 1.9 mmol) was added to a solution of 8 (375 mg, 0.63 mmol) in CHCl$_3$ (2.5 mL) and the resulting mixture was stirred at 60° C. for 22 h, after which volatiles were evaporated under reduced pressure. The crude was suspended with Et$_2$O and filtered under reduced pressure leading to the dimaleamic acid as a dark red solid that was used in the next step without further purification. The dimaleamic acid was dissolved in Ac$_2$O (16 mL) and then NaOAc (129 mg, 1.57 mmol) was added to the solution. The resulting mixture was then heated to 80° C. for 2 h, after which the volatiles were evaporated under reduced pressure. The crude product was then purified by flash chromatography on silica gel giving YC27 as a red solid (226 mg, 44% yield). $^1$H NMR (400 MHz, CDCl$_3$): δ (ppm) 7.51, (s, 7H), 7.34 (s, 1H), 6.85 (d, J=4.4 Hz, 1H), 6.77 (d, J=4.0 Hz, 1H), 6.53 (d, J=4.6 Hz, 1H), 6.30 (d, J=4.2 Hz, 1H), 5.53 (s, 2H), 3.97 (s, 6H), 3.79 (s, 2H), 3.76 (s, 3H), 1.50 (s, 9H); $^{13}$C NMR (100 MHz, CDCl$_3$): δ (ppm) 168.71, 168.16, 163.68, 160.62, 158.73, 148.87, 142.43, 136.51, 133.13, 131.67, 131.45, 130.58, 130.27, 129.71, 128.34, 121.50, 119.84, 118.35, 118.01, 96.57, 83.12, 59.09, 53.02, 34.43, 30.21, 28.06; $^{19}$F NMR (376.7 MHz, CDCl$_3$): δ (ppm) −145.84 (s); LRMS (ESI) m/z: 836.0 ([M+Na]$^+$); HRMS (ESI): calcd for C$_{39}$H$_{34}$BF$_2$N$_5$NaO$_{10}$S: 836.1992, found: 836.2169.

7-((3,5-bis(3-methoxy-2,5-dioxo-2,5-dihydro-1H-pyrrol-1-yl)phenyl)amino)-5,5-difluoro-3-((2-methoxy-2-oxoethyl)thio)-10-phenyl-5H-dipyrrolo[1,2-c:2',1'-f][1,3,2]diazaborinin-4-ium-5-uide (YC28)

To a solution of Compound YC27 (35 mg, 0.043 mmol) in toluene (1 mL) before was added DIPEA (77 μL, 0.43 mmol) and BF$_3$ etherate (83 μL, 0.67 mmol). The reaction mixture was stirred at r.t. for 20 min until TLC showed the complete consumption of compound YC27. The reaction was quenched by water and extracted with DCM, the organic phase was washed with H$_2$O and brine, dried over MgSO$_4$ and evaporated to dryness. The residue was purified by column chromatography to obtain YC28. $^1$H NMR (400 MHz, CDCl$_3$): δ (ppm) 7.71, (s, 1H), 7.56 (m, 7H), 6.90 (s, 2H), 6.55 (s, 1H), 6.01 (s, 1H), 5.59 (s, 2H), 4.00 (s, 6H), 3.85 (s, 2H), 3.77 (s, 3H); $^{13}$C NMR (100 MHz, CDCl$_3$): δ (ppm): 169.21, 167.87, 163.47, 160.76, 152.82, 148.51, 147.92, 139.59, 137.22, 136.11, 133.07, 132.74, 130.52, 130.36, 129.34, 128.67, 128.46, 128.23, 123.55, 121.96, 117.90, 109.16, 96.75, 59.27, 52.85, 35.54; $^{19}$F NMR (376.7 MHz, CDCl$_3$): δ (ppm) −139.47 (m); LRMS (ESI) m/z: 736.2 ([M+Na]$^+$); HRMS (ESI): calcd for C$_{34}$H$_{26}$BF$_2$N$_5$NaO$_8$S: 736.1467, found: 736.1492.

Synthesis of YC29

The synthetic route for the preparation of fluorogen YC29 is shown in Scheme 4.

Scheme 4. Synthetic route for the preparation of fluorogen YC29.

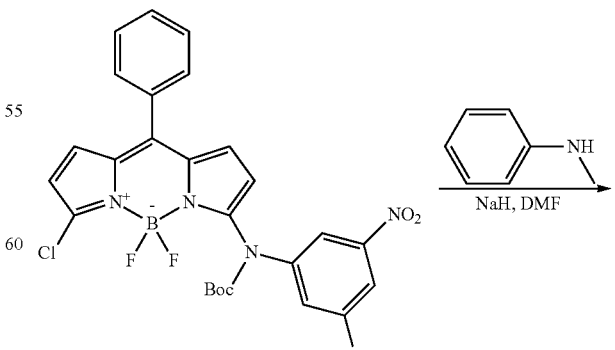

6

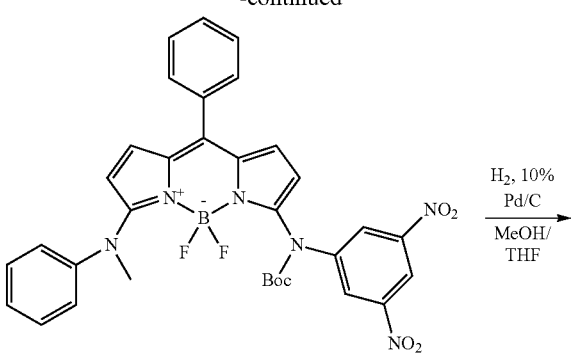
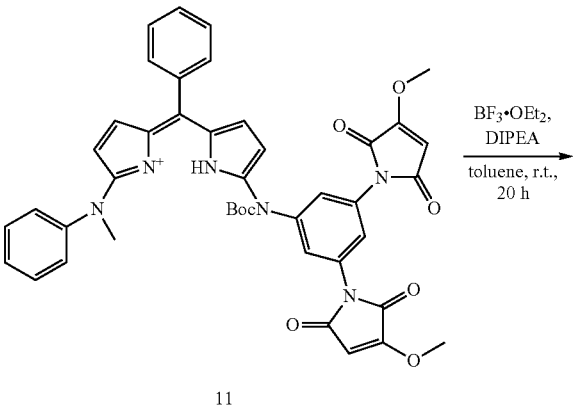
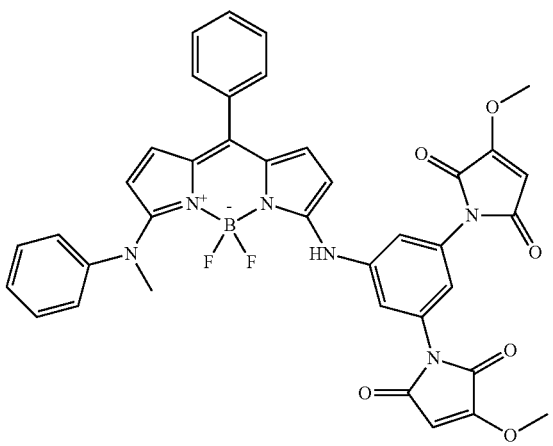

7-((tert-butoxycarbonyl)(3,5-dinitrophenyl)amino)-5,5-difluoro-3-(methyl(phenyl)amino)-10-phenyl-5H-dipyrrolo[1,2-c:2',1'-f][1,3,2]diazaborinin-4-ium-5-uide (9)

To a cooled solution of compound 6 (466 mg, 0.8 mmol) and N-methylaniline (173 μL, 1.6 mmol) in DMF was added NaH (35 mg, 0.88 mmol) in small portions. After the bubbling ceased, the reaction mixture was warmed up to 68° C. and stirred for 3 h. After the reaction was cooled down to room temperature, $NH_4Cl$ (aq) was added and the aqueous phase was extracted with EtOAc. The organic phase was washed with 0.1 N HCl, brine, dried over $MgSO_4$ and concentrated. The residue was purified by flash column chromatography to obtain compound 9 (204 mg, 39% yield). $^1H$ NMR (400 MHz, $CDCl_3$): δ (ppm) 8.66 (s, 1H), 8.64 (s, 2H), 7.34 (m, 10H), 6.63 (d, J=5.1 Hz, 1H), 6.33 (d, J=3.6 Hz, 1H), 6.23 (d, J=3.6 Hz, 1H), 5.58 (d, J=5.1 Hz, 1H), 3.76 (s, 3H), 1.47 (s, 9H); $^{13}C$ NMR (100 MHz, $CDCl_3$): δ (ppm) 163.64, 152.93, 148.04, 146.53, 145.61, 137.00, 136.23, 134.42, 134.39, 131.68, 130.55, 130.37, 130.25, 129.11, 128.50, 128.21, 126.62, 123.57, 117.75, 117.57, 113.41, 112.19, 83.24, 60.40, 43.61, 43.49, 43.36, 28.03, 21.06, 14.22; $^{19}F$ NMR (376.7 MHz, $CDCl_3$): δ (ppm) −126.20, −130.93; LRMS (ESI) m/z: 677.3 ([M+Na]$^+$); HRMS (ESI): calcd for $C_{33}H_{29}BF_2N_6NaO_6$: 677.2114, found: 677.2994.

7-((tert-butoxycarbonyl)(3,5-diaminophenyl)amino)-5,5-difluoro-3-(methyl(phenyl)amino)-10-phenyl-5H-dipyrrolo[1,2-c:2',1'-f][1,3,2]diazaborinin-4-ium-5-uide (10)

Compound 9 (182 mg, 0.28 mmol) was dissolved in MeOH/THF (2 mL/2 mL), the solution was purged with $N_2$ for 15 min. Pd/C (9 mg, 5% m/m) was added to the solution. The reaction mixture was stirred under $H_2$ for overnight. The finished reaction mixture was filtered through celite to remove Pd/C and the filtrate was evaporated to dryness. The residue was purified by short flash column chromatography to obtain compound 10 (48 mg, 29% yield). $^1H$ NMR (400 MHz, $CDCl_3$): δ (ppm) 7.35 (m, 10H), 6.61 (d, J=5.1 Hz, 1H), 6.33 (s, 3H), 6.13 (d, J=3.8 Hz, 1H), 5.83 (s, 1H), 5.59 (d, J=5.1 Hz, 1H), 3.74 (s, 3H), 1.49 (s, 9H); $^{13}C$ NMR (100 MHz, $CDCl_3$): δ (ppm) 163.54, 154.12, 147.20, 146.99, 144.67, 142.30, 135.29, 134.90, 133.34, 132.52, 130.56, 130.07, 129.58, 128.83, 128.03, 127.91, 126.62, 118.86, 116.39, 111.91, 103.41, 99.25, 84.15, 60.40, 51.26, 43.50, 43.43, 43.37, 43.32, 43.25, 28.23, 21.37, 17.28, 14.21; $^{19}F$ NMR (376.7 MHz, $CDCl_3$): δ (ppm) −125.42, −131.43; LRMS (ESI) m/z: 617.4 ([M+Na]$^+$); HRMS (ESI): calcd for $C_{33}H_{33}BF_2N_6NaO_2$: 617.2630, found: 617.2628.

(Z)-tert-butyl (3,5-bis(3-methoxy-2,5-dioxo-2,5-dihydro-1H-pyrrol-1-yl)phenyl)(5-((5-(methyl(phenyl)amino)-2H-pyrrol-2-ylidene)(phenyl)methyl)-1H-pyrrol-2-yl)carbamate (11)

Methoxymaleic anhydride (154 mg, 1.2 mmol) was added to a solution of 10 (240 mg, 0.4 mmol) in $CHCl_3$ (2.5 mL) and the resulting mixture was stirred at 60° C. for 22 h, after which volatiles were evaporated under reduced pressure. The crude was suspended with $Et_2O$ and filtered under reduced pressure leading to the dimaleamic acid as a dark red solid that was used in the next step without further purification. The dimaleamic acid was dissolved in $Ac_2O$ (10 mL) and then NaOAc (82 mg, 1 mmol) was added to the solution. The resulting mixture was then heated to 80° C.

overnight, after which the volatiles were evaporated under reduced pressure. The crude product was then purified by flash chromatography on silica gel giving 11 as a red solid (34 mg, 11% yield). $^1$H NMR (400 MHz, CDCl$_3$): δ (ppm) 13.54 (br, 1H), 7.71 (s, 1H), 7.39 (m, 13H), 6.68 (d, J=6.2 Hz, 1H), 6.18 (d, J=6.0 Hz, 1H), 5.98 (d, J=4.9 Hz, 1H), 5.59 (s, 2H), 5.43 (d, J=4.5 Hz, 1H), 4.01 (s, 6H), 3.80 (s, 3H), 1.49 (s, 9H); $^{13}$C NMR (75.48 MHz, CDCl$_3$): δ (ppm) 168.06, 166.37, 163.63, 160.69, 151.82, 145.87, 141.03, 137.95, 136.88, 136.21, 132.07, 131.01, 129.12, 127.60, 127.43, 125.21, 125.15, 124.08, 120.70, 117.22, 116.00, 100.09, 96.61, 82.73, 59.20, 39.25, 27.99; LRMS (ESI) m/z: 767.4 ([M+H]$^+$); HRMS (ESI): calcd for C$_{43}$H$_{39}$BN$_6$O$_8$: 767.2824, found: 767.4159.

7-((3,5-bis(3-methoxy-2,5-dioxo-2,5-dihydro-1H-pyrrol-1-yl)phenyl)amino)-5,5-difluoro-3-(methyl(phenyl)amino)-10-phenyl-5H-dipyrrolo[1,2-c:2',1'-f][1,3,2]diazaborinin-4-ium-5-uide (YC29)

To a solution of compound 11 (34 mg, 0.044 mmol) in toluene (1 mL) was added DIPEA (77 μL, 0.44 mmol) and BF$_3$ etherate (83 μL, 0.67 mmol). The reaction mixture was stirred at room temperature (r.t.) for 20 hours. The reaction was then quenched by water and extracted with DCM, the organic phase was washed with H$_2$O and brine, dried over MgSO$_4$ and evaporated to dryness. The residue was purified by column chromatography to obtain YC29. $^1$H NMR (400 MHz, CDCl$_3$): δ (ppm) 7.63, (t, J=1.9 Hz, 1H), 7.58 (d, J=1.9 Hz, 2H), 7.45 (m, 10H), 6.61 (dd, J=5.0, 2.0 Hz, 1H), 6.04 (d, J=4.2 Hz, 1H), 5.87 (dd, J=5.0, 1.8 Hz, 1H), 5.56 (s, 1H), 5.48 (d, J=4.2 Hz, 1H), 3.99 (s, 6H), 3.69 (s, 3H); $^{13}$C NMR (125.76 MHz, CDCl$_3$): δ (ppm) 167.95, 163.48, 160.64, 157.40, 148.88, 147.96, 143.09, 140.22, 138.80, 137.65, 137.23, 132.61, 132.43, 131.22, 130.20, 129.68, 129.46, 128.34, 127.82, 127.45, 125.71, 124.17, 121.23, 108.16, 100.79, 96.60, 59.16; $^{19}$F NMR (376.7 MHz, CDCl$_3$): δ (ppm) −135.74 (m); LRMS (ESI) m/z: 715.4 ([M+H]$^+$); HRMS (ESI): calcd for C$_{38}$H$_{30}$BF$_2$N$_6$O$_6^+$: 715.2288, found: 715.4802.

TABLE 1

| Abbreviations. | |
| --- | --- |
| ACN | acetonitrile |
| Ac$_2$O | acetic anhydride |
| AcOH | acetic acid |
| aq | aqueous |
| Boc | tert-butoxycarbonyl |
| calcd | calculated |
| DCE | dichloroethane |
| DCM | dichloromethane |
| DIPEA | diisopropylethylamine |
| DMAP | 4-dimethylaminopyridine |
| DMF | N,N-dimethylformamide |
| DMP | Dess-Martin periodinane |
| DMSO | dimethyl sulfoxide |
| EDC•HCl | N-ethyl-N'-(3-dimethylaminopropyl)carbodiimide hydrochloride |
| EI | electron ionization |
| em | emission |
| eq or equiv | equivalence |
| ESI | electrospray ionization |
| EtOAc or EA | ethyl acetate |
| Et | ethyl |
| EtO or OEt | ethoxy |
| ex | excitation |
| GSH | glutathione |
| h | hour |
| HEK | human embryonic kidney |
| HEPES | 4-(2-hydroxyethyl)-1-piperazineethanesulfonic acid |

TABLE 1-continued

| Abbreviations. | |
| --- | --- |
| HMDS | hexamethyldisilazane |
| HOBt | hydroxybenzotriazole |
| HRMS | high-resolution mass spectrometry |
| iPr | isopropyl |
| LRMS | low-resolution mass spectrometry |
| MBP | maltose-binding protein |
| Me | methyl |
| MeO or OMe | methoxy |
| MTT | 3-(4,5-dimethylthiazol-2-yl)-2,5-diphenyltetrazolium bromide |
| NMR | nuclear magnetic resonance |
| OiPr | isopropoxy |
| PeT | photoinduced electron transfer |
| Ph | phenyl |
| POI | protein of interest |
| r.t. | room temperature |
| sat. | saturated |
| mean ± SD | standard deviation of the mean |
| TBTU | N,N,N',N'-tetramethyl-O-(benzotriazol-1-yl)uronium tetrafluoroborate |
| THF | tetrahydrofuran |
| TEA | triethylamine |
| TFA | trifluoroacetic acid |
| Tol | toluene |

Although this invention is described in detail with reference to embodiments thereof, these embodiments are offered to illustrate but not to limit the invention. It is possible to make other embodiments that employ the principles of the invention and that fall within its spirit and scope as defined by the claims appended hereto.

The contents of all documents and references cited herein are hereby incorporated by reference in their entirety.

What is claimed is:

1. A fluorogenic labelling agent comprising a compound of Formula I, or a salt thereof:

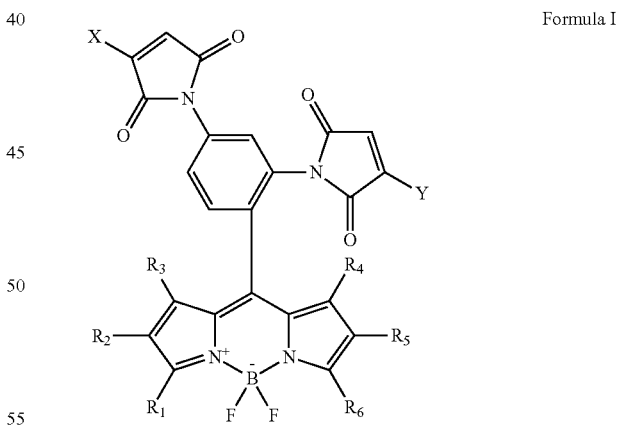

Formula I wherein:

R$_1$, R$_2$, R$_3$, R$_4$, R$_5$, and R$_6$ are independently selected from hydrogen, substituted or unsubstituted alkyl, alkenyl, alkynyl, cycloalkyl, cycloalkenyl, cycloalkynyl, aryl, alkaryl, arylalkyl, carboxy alkyl, heterocyclic, and heteroaryl; and X and Y are independently R$_7$ or OR$_8$, wherein R$_7$ is selected from hydrogen, halogen, and substituted or unsubstituted alkyl and R$_8$ is substituted or unsubstituted alkyl.

2. The fluorogenic labelling agent of claim 1, wherein:
at least one of X and Y is $OR_8$;
when one of X and Y is $OR_8$, then the other is $R_7$;
X and Y are the same;
X and Y are both $OR_8$, optionally wherein $R_8$ is alkyl, and optionally wherein X and Y are both methoxy; or
$R_7$ and $R_8$ are the same.

3. The fluorogenic labelling agent of claim 1, wherein $R_1$, $R_2$, $R_3$, $R_4$, $R_5$, and $R_6$ are independently selected from hydrogen and alkyl.

4. The fluorogenic labelling agent of claim 3, wherein:
$R_2$ and $R_5$ are hydrogen and $R_1$, $R_3$, $R_4$, and $R_6$ are alkyl, optionally wherein said alkyl is methyl; or
$R_1$, $R_2$, $R_3$, $R_4$, $R_5$, and $R_6$ are hydrogen.

5. The fluorogenic labelling agent of claim 1, wherein said fluorogenic labelling agent comprises a compound of Formula II, or a salt thereof:

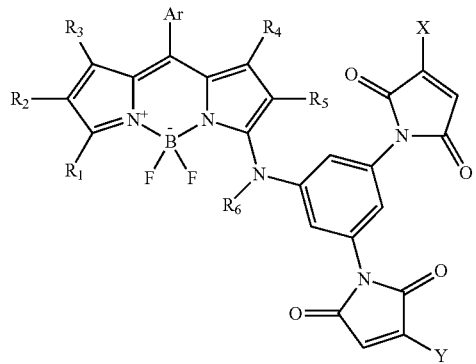

Formula II wherein:
$R_1$ is hydrogen, $R_1'$, $SR_1'$, $OR_1'$ or $NR_2'R_3'$, wherein $R_1'$, $R_2'$ and $R_3'$ are independently selected from hydrogen, substituted or unsubstituted alkyl, alkenyl, alkynyl, cycloalkyl, cycloalkenyl, cycloalkynyl, aryl, alkaryl, arylalkyl, and carboxy alkyl; or $R_1'$ and $R_2$ or $R_1'$ and $R_3$ come together to form a 5, 6 or 7-membered ring which is selected from aryl, heterocyclic, and heteroaryl; or $R_2'$, $R_2$, $R_3'$, and $R_3$ come together independently to form at least one 5, 6 or 7-membered ring which is selected from aryl, heterocyclic, and heteroaryl;
$R_2$, $R_3$, $R_4$, $R_5$ and $R_6$ are independently selected from hydrogen, substituted or unsubstituted alkyl, alkenyl, alkynyl, cycloalkyl, cycloalkenyl, cycloalkynyl, aryl, alkaryl, arylalkyl, carboxy alkyl, heterocyclic, and heteroaryl;
X and Y are independently $R_7$ or $OR_8$, wherein $R_7$ is selected from hydrogen, halogen, and substituted or unsubstituted alkyl, and $R_8$ is substituted or unsubstituted alkyl; and
Ar is substituted or unsubstituted aryl, substituted or unsubstituted heterocyclic, or substituted or unsubstituted heteroaryl.

6. The fluorogenic labelling agent of claim 5, wherein:
at least one of X and Y is $OR_8$;
when one of X and Y is $OR_8$, then the other is $R_7$;
X and Y are the same;
X and Y are both $OR_8$, optionally wherein $R_8$ is alkyl; or
$R_7$ and $R_8$ are the same, optionally wherein both X and Y are methoxy.

7. The fluorogenic labelling agent of claim 5, wherein:
$R_2$, $R_3$, $R_4$, $R_5$ and $R_6$ are hydrogen;
$R_1$ is $R_1'$, $SR_1'$, $OR_1'$ or $NR_2'R_3'$;
$R_1$ is an amino substituent, an oxygen substituent, a sulfur substituent, a thiol ether, or an ester; or
$R_1$ is selected from hydrogen, $MeO_2CCH_2S$, and NMePh.

8. The fluorogenic labelling agent of claim 5, wherein Ar is phenyl, pyridine, pyrimidine or triazine and is optionally substituted by alkyl, cycloalkyl or halogen, alkyl being optionally substituted with hydroxyl, amino, carboxyl, sulfonate, carboxylic ester, amide, carbamate, or aminoalkyl.

9. The fluorogenic labelling agent of claim 1, wherein said fluorogenic labelling agent comprises a compound selected from YC23, YC28, and YC29:

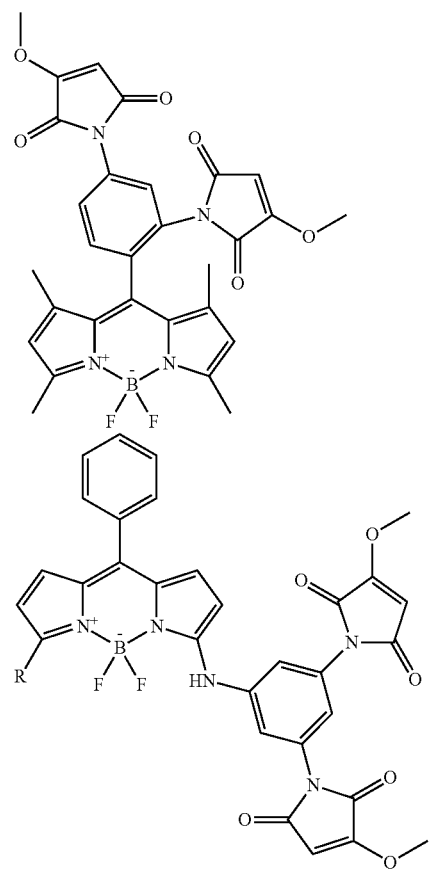

YC23

YC28 (R = $MeO_2CCH_2S$)
YC29 (R = NMePh)

or a salt thereof.

10. The fluorogenic labelling agent of claim 1, wherein the fluorogenic labelling agent is not toxic to animal cells.

11. The fluorogenic labelling agent of claim 10, wherein the animal cells are mammalian cells, invertebrate cells, vertebrate cells, human cells, rodent cells, mouse cells, rat cells, insect cells, nematode cells, or fish cells.

12. The fluorogenic labelling agent of claim 1, wherein the fluorogenic labelling agent's fluorescence is quenched when the fluorogenic labelling agent is in its conjugated form, and not quenched in the form of a thiol adduct, or wherein the fluorescence of the fluorogenic labelling agent increases after reaction with sulfhydryl groups on a protein.

13. The fluorogenic labelling agent of claim 1, wherein the fluorogenic labelling agent specifically reacts with two Cys residues separated by about 10 Å or a dC10α tag, or wherein the fluorogenic labelling agent does not react appreciably with cellular proteins or with glutathione (GSH).

14. The fluorogenic labelling agent of claim 1, wherein the fluorogenic labelling agent has one or more of the following characteristics: aqueous solubility; non-toxic to animal cells; low background fluorescence before reaction with a target protein; increased fluorescence after reaction with a target protein; bright fluorescence after reaction with a target protein; cell permeability; non-reactivity with GSH; and specific binding to two sulfhydryl residues separated by about 10 Å or a dC10α tag.

15. The fluorogenic labelling agent of claim 1, wherein the fluorogenic labelling agent is visible by fluorescent microscope using the green or red channel.

16. A method for labelling and/or detecting a target protein, comprising:
    a) contacting the target protein with the fluorogenic labelling agent of claim 1, under conditions where the fluorogenic labelling agent reacts with sterically unhindered sulfhydryl groups on the target protein; and
    b) detecting a fluorescent signal from the fluorogenic labelling agent,
    wherein the fluorescence of the fluorogenic labelling agent is quenched in the absence of reaction with the target protein, and detection of the fluorescent signal indicates that reaction of the fluorogenic labelling agent with the target protein, or wherein the fluorescence of the fluorogenic labelling agent increases after reaction with the target protein.

17. The method of claim 16, wherein said contacting occurs in vivo, ex vivo, or in vitro.

18. The method of claim 16, wherein the target protein comprises two Cys residues separated by about 10 Å or comprises a dC10α tag.

19. The method of claim 16, wherein the target protein has been genetically engineered to comprise two Cys residues separated by about 10 Å or a dC10α tag.

20. The method of claim 16, wherein said contacting occurs in a cultured cell expressing the target protein, wherein said target protein is an intracellular protein, an extracellular protein, or a cell-surface protein, optionally wherein said contacting occurs intracellularly.

21. A method for live imaging of a target protein, comprising:
    a) contacting the target protein with the fluorogenic labelling agent of claim 1, under conditions where the fluorogenic labelling agent reacts with sterically unhindered sulfhydryl groups on the target protein; and
    b) detecting a fluorescent signal from the fluorogenic labelling agent,
    wherein the fluorescence of the fluorogenic labelling agent increases after reaction with the target protein, or is detectable only after reaction with the target protein.

22. The method of claim 21, wherein the target protein has been engineered to comprise two Cysteine residues separated by about 10 Å or a dC10α tag prior to said contacting.

23. A kit for labelling and/or detecting a target protein, the kit comprising the fluorogenic labelling agent of claim 1, and instructions for use thereof.

* * * * *